(12) United States Patent
Garver et al.

(10) Patent No.: US 6,263,725 B1
(45) Date of Patent: Jul. 24, 2001

(54) ON-LINE SENSOR FOR COLLOIDAL SUBSTANCES

(75) Inventors: Theodore M. Garver, Edmonton; Kenneth Bough, Thunder Bay, both of (CA)

(73) Assignee: Alberta Research Council Inc., Edmonton (CA)

( * ) Notice: Subject to any disclaimer, the term of this patent is extended or adjusted under 35 U.S.C. 154(b) by 0 days.

(21) Appl. No.: 09/422,269

(22) Filed: Sep. 18, 1998

(51) Int. Cl.$^7$ .......................... G01N 15/06; G01N 21/49
(52) U.S. Cl. .................. 73/61.71; 73/61.48; 73/53.03; 250/372; 250/373; 356/441; 356/442
(58) Field of Search ................. 73/53.03, 61.48, 73/61.71; 162/49, 50; 250/372, 373; 356/441, 442

(56) References Cited

U.S. PATENT DOCUMENTS

| | | |
|---|---|---|
| 4,318,180 | 3/1982 | Lundqvist et al. . |
| 4,752,131 | 6/1988 | Eisenlauer et al. . |
| 4,791,305 | 12/1988 | Karaila . |
| 4,999,514 | 3/1991 | Silveston . |
| 5,331,177 | 7/1994 | Kubisiak et al. . |
| 5,453,832 | 9/1995 | Joyce . |
| 6,023,065 | * 2/2000 | Garver, Jr. ................. 250/372 |

FOREIGN PATENT DOCUMENTS

| | | |
|---|---|---|
| 2106472 | 3/1992 | (CA) . |
| 2174432 | 10/1994 | (CA) . |

* cited by examiner

*Primary Examiner*—Daniel S. Larkin
(74) *Attorney, Agent, or Firm*—Freedman & Associates

(57) ABSTRACT

A method and apparatus are for characterizing colloids by successive measurements of light attenuation or emission of a colloidal mixture at two or more temperatures and at one or more wavelengths. The difference or ratio of the measurements at two or more temperatures provides a measure of the colloidal stability with respect to temperature. The amount of certain organic colloids that are unstable to temperature variation may be determined from the magnitude of the measurement change. In appropriate mixtures, this method provides a means to distinguish components of colloidal substances based. This method may be specifically applied to determining the stability and concentration of colloidal pitch or wood resin in a pulp or paper process water. In this context it may be used to distinguishing colloidal pitch or wood resin from talc, clay, carbon black, or other fillers.

27 Claims, 21 Drawing Sheets

ON-LINE SENSOR FOR COLLOIDAL SUBSTANCES

FIELD OF THE INVENTION

This invention relates to the application of ultraviolet-visible light measurements for the determination of colloidal substances in a liquid sample. More particularly, the invention relates to the application of light absorption and/or scattering measurements for determining a property of colloidal substances that undergo a temperature dependent phase transition.

BACKGROUND OF THE INVENTION

Papermaker's demands for high speed and efficiency, flexible manufacturing, stringent quality standards, and environmental compatibility coupled with new developments in on-line process control are driving the development of new sensor technology for the paper machine wet-end. The need for better means for providing wet-end chemistry control is emphasized by recent reports that only 10% of the world's one hundred fifty newsprint paper machines operate at above 88% efficiency and over 60% operate under in the low efficiency range of below 82.5%. (Mardon, J., Chinn, G. P., O'Blenes, G., Robertson, G., Tkacz, A. Pulp and Paper Canada, Vol. 99 No. 5 pp. 43–46. (1998).

William E. Scott addressed problems related to wet-end chemistry control. *Principles of Wet End Chemistry.* Tappi Press, Atlanta, 1996. p 3. "Deposits and scale usually arise from out-of-control wet end chemistry. Typical examples include chemical additive overdosing, charge imbalances, chemical incompatibility, and the shifting of chemical equilibria. All of these phenomena can lead to the formation of precipitates or colloidal aggregates that produce deposits and scale. While there are numerous approaches to treating the symptoms of deposits, the best approach is to determine what is out of control and fix it."

Although variations in the composition and quantity of dissolved solids can lead to problems throughout the paper mill, it is particularly important at the wet-end of the paper machine where the colloidal chemistry must be tuned for optimal machine performance. It is important to gain knowledge and understanding of the relationship between measurements at both the point of origin (pulp mills, bleaching points) and the point of impact (headbox, press-section of the paper machine).

The measurement and characterization of colloidal particles distributed in a liquid stream is an important function in the control of industrial processes involving heterogeneous mixtures. Examples of such processes include pulping and papermaking, water treatment, brewing and food processing, chemical synthesis, and manufacturing. Although numerous methods are available to characterize colloid size and concentration, methods to measure the amount of different colloids components mixed together or to rapidly evaluate the temperature stability of the colloid suspension are not readily available.

Measurements relating the intensity and angular dependence of scattered or absorbed light to the total concentration or size distribution of colloids are available in numerous forms. Instruments for characterizing the amount of colloidal particles that rely on scattering (nepholometry) and attenuation (turbidimetry) are commercially available in laboratory, hand-held, and on-line instruments. On line turbidimeters relate a ratio of light detected in line and at an angle to a source to a turbidity value in Jackson or NTU units. Silveston, U.S. Pat. No. 4,999,514, taught methods for controlling the intensity of the light source to provide a turbidimeter that operates over a broad range of particle concentrations. Kubisiak and Wilson (U.S. Pat. No. 5,331, 177) describe an analog to digital turbitimeter apparatus that provides a measure of the change in turbidity over time. Other, more sophisticated, methods involving the analysis of the time and spatial dependence of light attenuation and scattering may provide information on particle size distributions as taught by Strickland et, (U.S. Pat. No. 5,576,827 and the patents referenced therein). Instrumentation specifically designed for measuring particle and fiber size distributions in low consistency (<1%) pulp suspensions by analysis of the time and spatial variation of scattered or absorbed light includes the BTG (British Technology Group) RET-5300 Retention Monitoring System. This instrument employs methods taught by Lundqvist, Pettersson, and Fladda, U.S. Pat. No. 4,318,180. The available instruments do not have a means to differentiate concentrations of similarly sized colloidal pitch particles from colloidal clay particles.

In the area of pulp and paper manufacture, the maintenance of a level of stability and removal of colloidal pitch is an important objective in the wet-end chemistry programs. Deposition leading to poor paper machine efficiency is a costly problem that is addressed through numerous strategies involving pulp processing or chemical addition. Polymer, clay, and talc additives are used to prevent pitch accumulation that may lead to deposition and fouling of pulp processing and papermaking equipment. For example, Cutts taught one method for controlling pitch using micro-particle bentonite addition with cationic polymer flocculation, U.S. Pat. No. 5,676,796. Another combination of using kaolin as inorganic colloid and poly(diallyldimethyl-ammonium chloride) cationic polymer has been taught by Lamar, Pratt, Weber, and Roeder (U.S. Pat. No. 4,964,955). Alternatively, Dreisbach and Barton taught (U.S. Pat. No. 5,266,166) a method of preventing pitch deposits by the addition of nonionic polymeric dispersing agent. A physical process for reducing wood resin pitch from wood process water employing a centrifuge has been taught by Allen and Lapointe (U.S. Pat. No. 5,468,396). The teachings of this invention review the sources and problems associated with wood resin in paper mills and provide further information on physical methods of reducing pitch in pulp and paper process waters.

Chemical and physical methods of controlling pitch may be monitored by turbidity or Zeta, or streaming potential, or charge measurements. Although surface charge or total charge are important measures of the colloidal stability, these measurements do not distinguish colloidal pitch from other, less problematic colloids, such as added clay. Furthermore, turbidity may provide a means of evaluating the total amount of colloidal substance, but pitch colloids are not normally distinguished from other colloids in a turbidity measurement. Typically, no instrumental means are employed to supervise chemical methods of controlling pitch. Despite the high cost of chemical treatment programs and the potential downtime caused by over or under dosing, chemical methods of controlling pitch are often invariant over time and substantial swings in wet-end chemistry.

There is no colloidal pitch measurement available on-line. The accepted laboratory method of pitch analysis using microscopy was taught by Allen (Allen, L. H., Trans. Tech Sect. CPPA 3(2):32 (1977)). This procedure is time consuming, as it has not yet been successfully automated by computerized image analysis techniques. An instrumental method employing a laser beam to count particles flowing through a capillary has been described by Eisenlauer, Horn, Ditter, Eipel, (U.S. Pat. No. 4,752,131). The laser method, known as a pitch counter, requires expensive and specialized instrumentation that is not easily adopted to analysis in an industrial setting.

It is an object of the invention to provide a method of identifying and measuring a characteristic of a colloidal mixture.

It is a further object of this invention to provide a method and means for the rapid determination of an amount of colloidal pitch.

Polychromatic light passed through a colloid sample and detected at an array of wavelengths is a complicated function of the light absorption of the liquid, the light absorption of the particles, the light emission by fluorescence from dissolved or colloidal components, and the scattering that may deflect light away from or towards the detector. The scattering of particles in the range of 0.1–10 times the wavelength of light (Mie scattering) is a complicated function of wavelength, particle size, concentration, and refractive index of the particles, and of the medium. Hence, when the absorption of the colloidal particles is examined, we are looking at both scattering and the UV absorbance of the particles. The wavelength dependence will be a function of the color of the particles, and also the size of the particles. Mie-scattering theory may be solved to back out the particle size distribution from the wavelength dependence of absorption or scattering for a pure or well-characterized substance. But the theory and the calculations are complex, and they are certainly can not be directly applied to analyzing heterogeneous industrial or pulp and paper colloids. The measurements described in this invention provide a means to empirically identify and measure a property related to the particle size, composition, and concentration of a colloidal mixture.

SUMMARY OF THE INVENTION

In accordance with the invention, there is provided a method for identifying and measuring a characteristic of a colloidal mixture comprising the steps of:

irradiating at least a first portion of the colloidal mixture with light in an ultraviolet-visible region at a first temperature and obtaining a first measurement of a first wavelength within the ultraviolet-visible region, said first measurement for obtaining a measure of said first wavelength is one of an absorption, an emission, and a scattering of the first wavelength when said colloidal mixture is irradiated with the light;

waiting for the temperature of the colloidal mixture to change;

irradiating at least a second portion of the colloidal mixture with light in an ultraviolet-visible region at a second different temperature and obtaining a second measurement of the first wavelength within the ultraviolet-visible region; said second measurement for obtaining a measure of said first wavelength is one of an absorption, an emission, and a scattering of the first wavelength when said colloidal mixture is irradiated with the light; and determining the characteristic of the colloidal mixture from a relationship including the first measurement and the second measurement.

In accordance with the invention, there is further provided a method for identifying and measuring a characteristic of a colloidal mixture comprising the steps of:

irradiating at least a first portion of the colloidal mixture with light in an ultraviolet-visible region at a first temperature and obtaining at least a first measurement of a first and a second wavelength within the ultraviolet-visible region, said first measurement for obtaining said first and second wavelength is one of an absorption, an emission, and a scattering of the first wavelength when said colloidal mixture is irradiated with the light;

waiting for the temperature of the colloidal mixture to change;

irradiating at least a second portion of the colloidal mixture with light in an ultraviolet-visible region at a second different temperature and obtaining at least a second measurement of the first and the second wavelength within the ultraviolet-visible region, said second measurement for obtaining said first and second wavelength is one of an absorption, an emission, and a scattering of the second wavelength when said colloidal mixture is irradiated with the light; and determining the characteristic of the colloidal mixture from a relationship including a ratio of the at least first and second measurement.

In accordance with another aspect of the invention, there is provided, an apparatus for identifying and measuring a characteristic of a colloidal mixture comprising:

filtration means for substantially removing fiber from the colloidal mixture;

detecting means for obtaining a first measurement and a second measurement of light in an ultraviolet-visible region, said first measurement is for obtaining a measure of one of an absorption, an emission, and a scattering of light at least a first wavelength at a first temperature when the colloidal mixture is irradiated with the light, and said second measurement is for obtaining a measure of one of an absorption, an emission, and a scattering of light at the first wavelength at a second different temperature when the colloidal mixture is irradiated with the light; and a suitably programmed processor for determining the characteristic of the colloidal mixture from a relationship including the first and second measurement, said characteristic is a function of a first or second derivative of the at least first and second measurement.

BRIEF DESCRIPTION OF THE DRAWINGS

Exemplary embodiments of the invention will now be described in accordance with the drawings in which.

DETAILED DESCRIPTION OF THE INVENTION

The method and the apparatus in accordance with the invention provides for on-line measurements of colloidal substances in a liquid sample. This invention is particularly useful for determining or estimating the amount of colloidal substances in pulp or paper mill process water or effluents.

Figure 1:
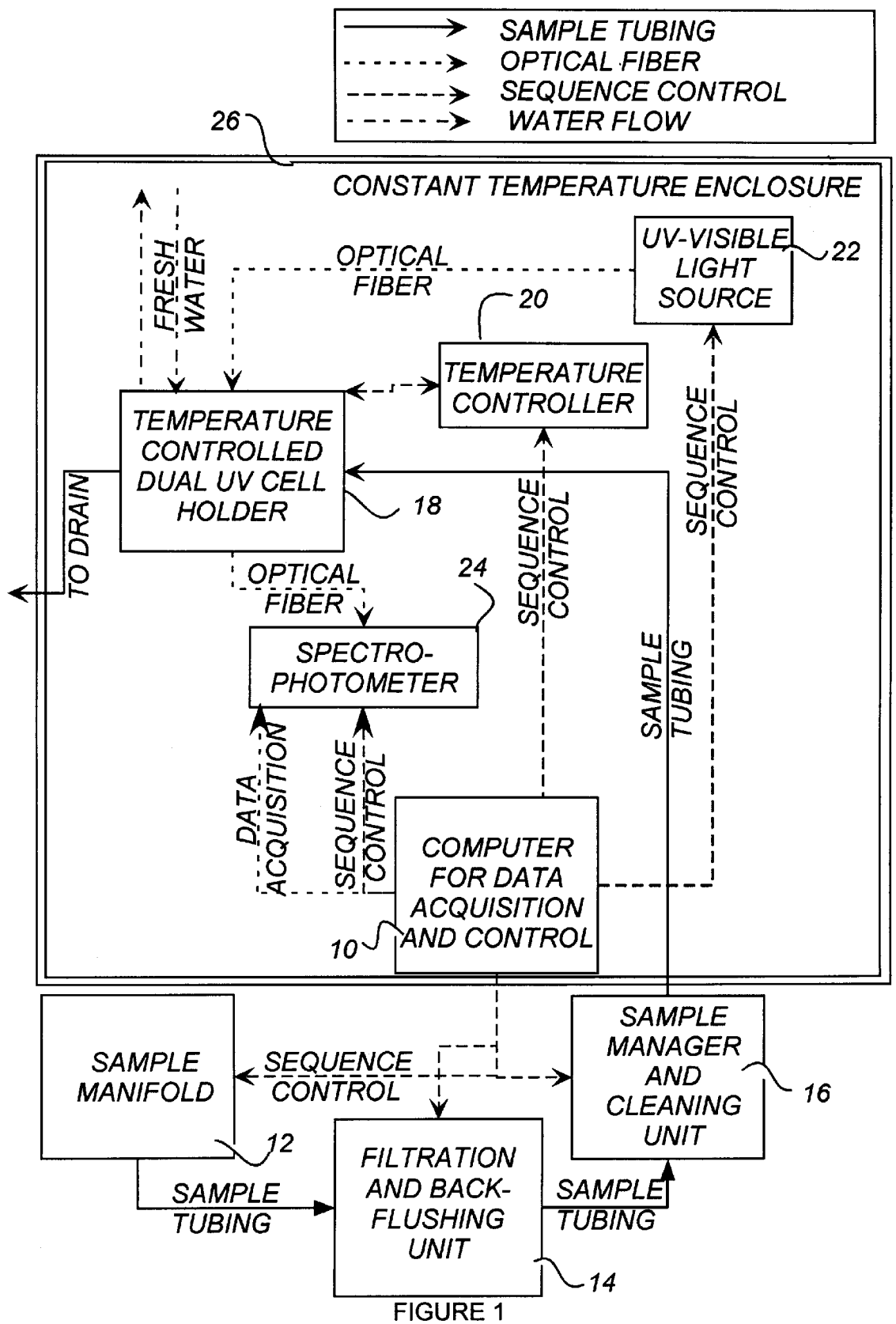
FIG. 1 presents a block diagram of an on-line sensor/apparatus for colloidal substances, as in accordance with the invention.

Referring now to FIG. 1, a block diagram of such an on-line sensor/apparatus for colloidal substances is depicted. In a preferred embodiment, the apparatus in agreement with the invention is controlled by a computer/processor 10 for sampling, filtration, data acquisition, cleaning, and temperature control.

In a preferred embodiment of the invention, the processor 10 has the following characteristics. The processor is a Computer-Micro-Alliance Industrial Computer with 14 slot chassis, 300W/ fans, 14" Industrial Rackmount monitor, and software, such as Labview for Windows Development System, Labview PID Control Toolkit, and PC-DIO and NI-DAQ Software. The input/output hardware used are National Instruments AT-MIO-16XE-50 Multifunction IO board (ISA card), National Instruments AT-AO-6; six channel analog output (ISA card) (this is for the 4–20 mA output to the temperature controller and the Distributed Control system), National Instruments NI DIO-24; twenty-four channel digital input/output (ISA card). This has all the output for the valves and input for the proximity sensors, and an Ocean Optics' ADC-500 A/D board with 500 kHz sampling frequency. This is for communication with the MQ-2000 spectrophotometer.

The sample tubing is shown as thick solid lines, the optical fibre is shown as thick dashed lines, the sequence control is shown as thin dashed lines, and the water flow is shown as thin solid lines. The processor 10 is connected to the sample manifold 12 for controlling the operation of a valve or a plurality of valves (not shown). In a preferred embodiment, six ball valves are actuated in sequence by the processor 10. The sample manifold 12 allows a plurality of water or pulp slurry samples to be sampled on-line from a process. The liquid sample is then delivered from the sample manifold 12 to the filtration and backflushing unit (FBU) 14. The FBU 14 filters the liquid sample to provide a fibre-free liquid sample and returns the remaining sample back into the process. The operation of this FBU 14 is also controlled by the processor 10 and is explained in more detail below, see FIG. 2.

The usefulness of the invention could be extended by extraction of liquid samples from a high consistency pulp slurry before final removal of the fiber in the FBU 14.

The FBU 14 delivers the fibre-free liquid sample to a sample manager and cleaning unit (SMCU) 16. The operation of the SMCU 16 is controlled by the processor 10. In one mode of operation, the SMCU 16 delivers the liquid sample to a temperature controlled dual UV cell holder (DUVCH) 18 for obtaining a UV measurement; and in another mode of operation, it delivers a cleaning fluid to the temperature controlled DUVCH 18 for cleaning said DUVCH. Both, the liquid sample and the cleaning fluid are delivered to the DUVCH 18 by means of a pump, such as a Cole Palmer variable speed peristaltic pump P-77962-10.

In a preferred embodiment, the DUVCH 18 has a Sciencetech custom-built cell holder and a temperature control unit with a Peltier Effect thermoelectric heat pump. This means that the DUVCH allows for UV measurements to be taken at a plurality of temperatures. Altenatively, the temperature in the DUVCH 18 is controlled by a water flow system, as shown in FIG. 1. The DUVCH has two UV cells, one 1.0 mm flowthrough quartz UV cell (UV region, short wavelength), and another 10.0 mm flow-through quartz UV cell (visible region, long wavelength). This is desired since the absorbance in the visible region is very low and requires a cell having a longer path length and vice versa, the absorbance in the UV region is very intense and a cell having a shorter path length is more desirable. The processor 10 controls the operation of a temperature controller 20. This temperature controller 20 is connected to the DUVCH 18 for controlling the temperature therein as. One possible temperature controller for use with this invention is a Wavelength Electronics Model LFI-3526 Temperature Controller.

The DUVCH 18 is connected to a UV-visible light source (UV-vis LS) 22, such as a Deuterium-Tungsten combination light source, and a spectrophotometer 24, such as a Rack Mount Ocean Optics spectrometer, through optical fibre cables suitable for good transmission of light at 230 nm. The UV-vis LS 22 irradiates the DUVCH 18 for obtaining a UV measurement of the liquid sample. The spectrophotometer 24 measures the UV light upon passing the liquid sample. The optical system, i.e. the UV-vis LS 22 and the spectrophotometer 24, are controlled by a Labview VI software.

The processor 10, the DUVCH 18, the temperature controller 20, the UV-vis LS 22, and the spectrophotometer 24 are placed within a constant temperature enclosure (CTE) 26, a Hoffmann Enclosure with air conditioning for temperature control. The CTE 26 prevents the apparatus from being effected by unwanted fluctuations in the temperature. This is done to prevent a possible damage to the processor 10 from excessive heat or humidity in industrial applications, such as in pulp and paper processing, and to obtain reproducible results. The CTE 26 is needed as in accordance with an embodiment of the invention because the response of spectrophotometer detector elements varies with temperature.

Exemplary Detector Specifications

Detector: 2048-element linear silicon CCD array

CCD elements: 2048 elements @ 12.5 mm ×200 mm per element

Well depth (@600 nm): 160,000 photons

Sensitivity (estimated):86 photons/count; 2.9×10–17 joule/count; 2.9×10–17 watts/count (for 1-second integration) Effective range: 200–1100 nm Integration time: four milliseconds to sixty seconds (with 500 kHz A/D card) twenty milliseconds to sixty seconds (with 100 kHz PCMCIA A/D card) (shorter integration times available with custom electronic interface)

Exemplary Optics Specifications

Gratings: multiple grating choices, optimized for UV, VIS, or Shortwave NIR

Slits: 10, 25, 50, 100, 200 mm widths (slit height is 1000 mm); alternative option is no slit (optical fiber is entrance aperture)

Order-sorting: single-piece, multi-bandpass detector coating for applications from ~200–850 mn (available only with 600-line gratings) or Schott glass longpass filters (installed or loose)

Resolution: ~0.3 nm–10.0 nm FWHM (depends on groove density of grating and diameter of fiber or width of slit)

Stray light: <0.05% at 600 nm; <0.10% at 435 nm

Fiber optic connector: SMA 905 to single-strand optical fiber (0.22 NA)

Exemplary Rack-mount Housing Specifications

Width: 17⅝"

Depth: 10⅙"

Weight: ~12 lb.*

* With eight spectrometer channels installed.

Exemplary Computer and Data Acquisition a) Computer-Micro-Alliance Industrial Computer with 14 slot chassis, 300W/ fans, b) Monitor. 14" Industrial Rackmount monitor.

c) software
  i) Labview for Windows Development System
  ii) Labview PID Control Toolkit
  iii) PC-DIO and NI-DAQ Software d) input/output hardware
  i) National instruments AT-MIO-16XE-50 Multifunction IO board (ISA card)
  ii) National Instruments AT-AO-6; six channel analog output (ISA card) (this is for the 4–20 mA output to the temperature controller and the Distributed Control system)
  iii) National Instruments NI DIO-24; twenty-four channel digital input/output (ISA card).
    (This has all the output for valves and input for the proximity sensors.)
  iv) Ocean Optics' ADC-500. A/D board with 500 kHz sampling frequency. This is for communication with the MQ-2000 spectrophotometer.

Figure 2:
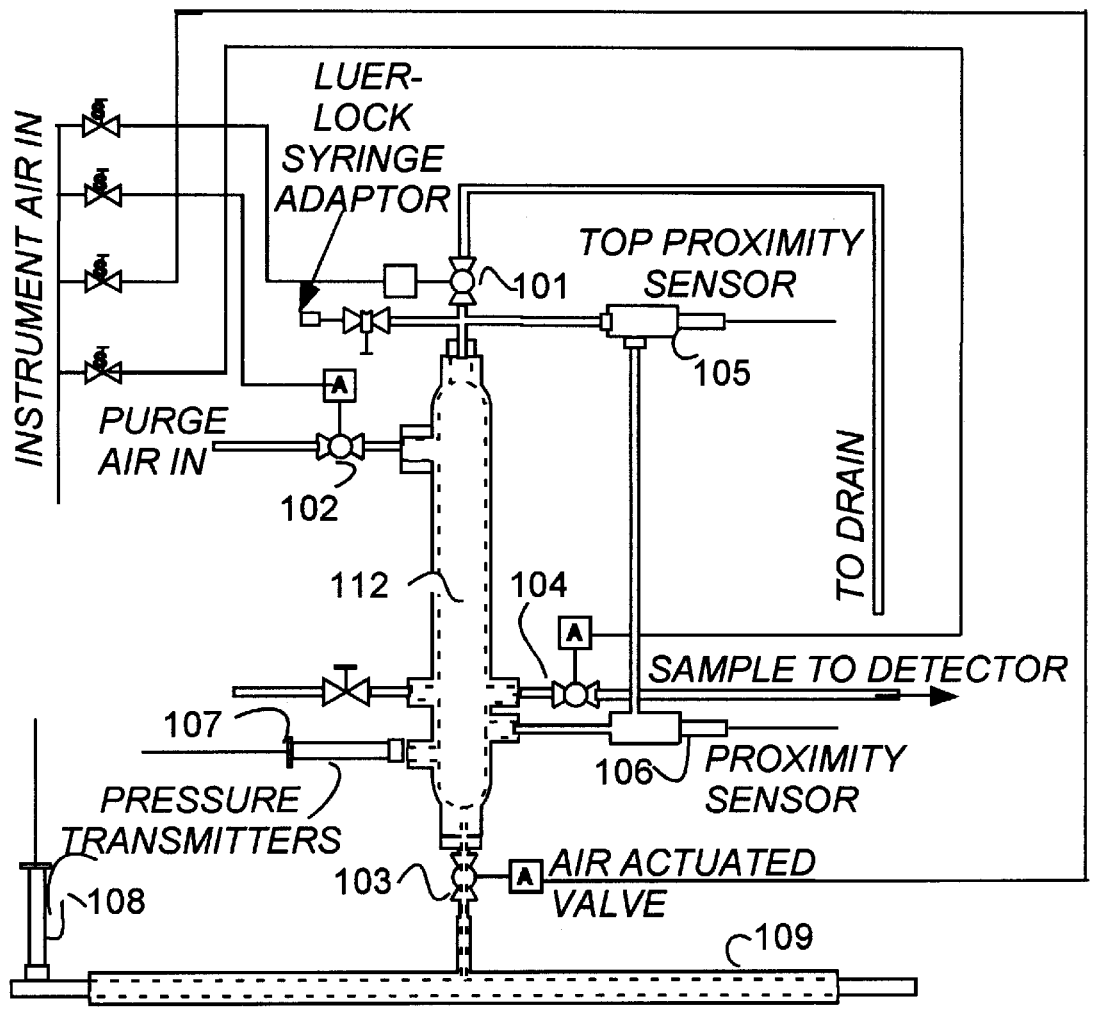
FIG. 2 shows a detailed schematic diagram of the filtration and backflushing unit, a currbackflushing apparatus for the Mott Filtration system.

Now turning to FIG. 2, the FBU 14 is presented in a more detailed manner. The FBU in FIG. 2 is a backflushing apparatus for the Mott Filtration system. The filtration and backflushing unit provides a fiber-free liquid sample. The colloidal liquid is separated from the fiber by cross-flow filtration using a five or ten micron Mott sintered metal filter 109. Tangential flow through the filter 109 is greater than twenty liters/minute and preferably greater than forty liters/min. The flow across the filter 109 is 10–200 ml/minute. The backflushing unit allows a reservoir 112 to fill with filtrate. Then, the sample valve 104 is opened for two seconds to deliver 1–20 ml of colloidal sample to the DUVCH 18. The sampling period is followed by a delay period during which the filter 109 is closed and temperature dependent UV measurements are made by the spectrophotometer 24 using the recently obtained sample. After the measuring delay, the reservoir 112 is purged by opening an air valve 102 (labeled purge air in) and backpulsing the filtrate backwards through the filter 109 for a specified period of at least one second, but no longer than, until the filtrate reaches the bottom proximity sensor 106. Backpulse pressure at pressure transmitter 107 is preferably greater than normal pressure measured at pressure transmitter 108. The bottom proximity sensor 106 relays a signal to the system controller/processor 10 to close the purge air valve 102 and open the reservoir vent valve 101. At this point, the filter valve 103 is opened and the reservoir 112 fills until the top proximity sensor 105 detects the filtrate. The full sample valve 104 immediately opens to obtain another sample of the colloid material.

Figure 3:
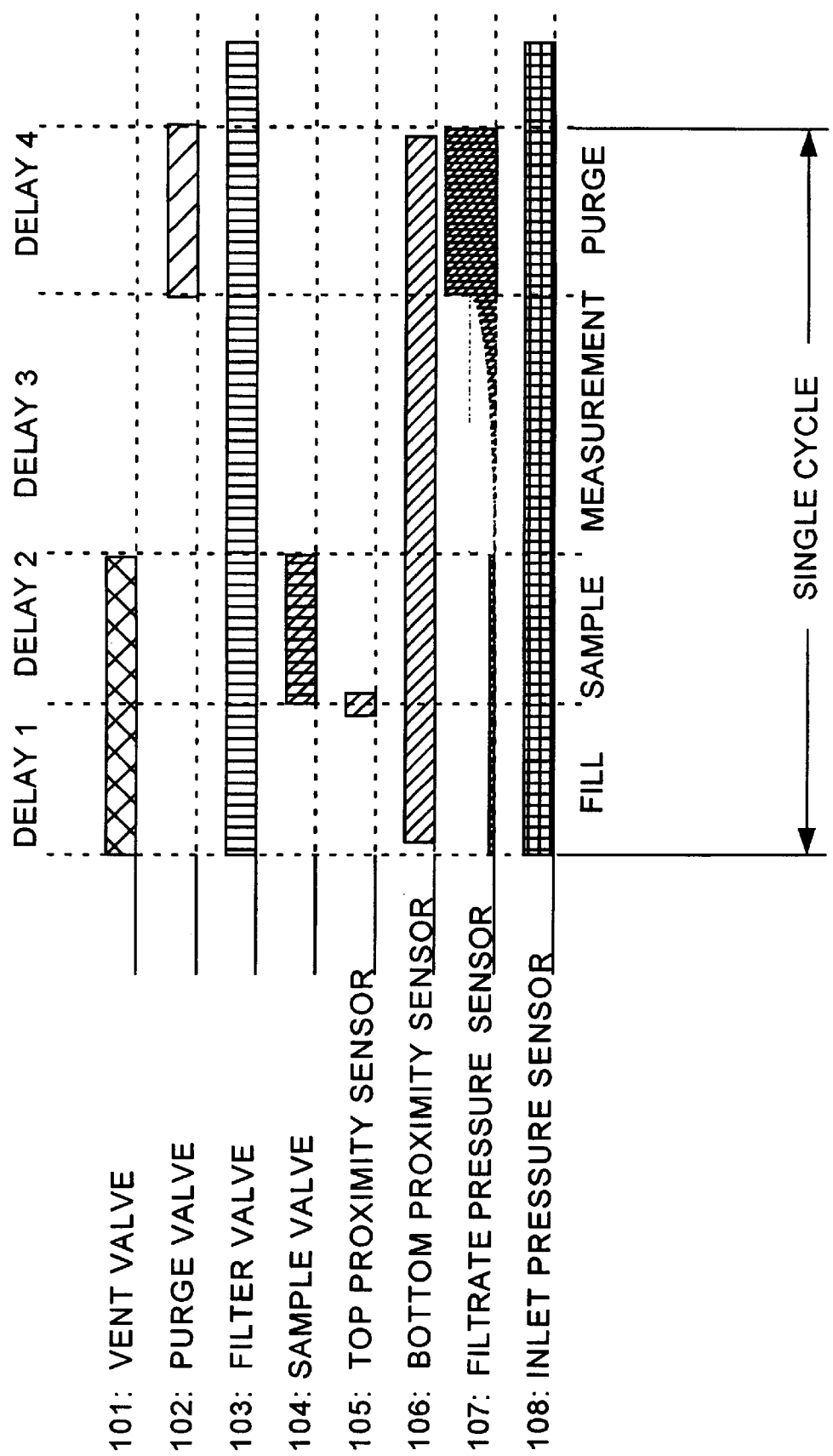
FIG. 3 is a timing diagram depicting the valve sequence of the filtration and backflushing unit.

The valve sequence is shown in FIG. 3 which is a detailed sketch of the operation of valves 101–104, the top proximity sensor 105, the bottom proximity sensor 106, the filtrate pressure sensor 107, and the inlet pressure sensor 108 for the various steps in a filtration and measurement cycle, such as filling, sampling, measurement, and purge.

There are a number of methods of obtaining a fiber-free colloidal sample. In a preferred method, a sample is obtained without filtering the liquid through a pulp mat or filter cake. It has been found that a pulp mat will significantly change the sample. Centrifugal methods are ideal, but continuous solids ejecting centrifuges are expensive. A sand filter will remove fiber, but the backwashing cycle would have to be frequent to prevent filtration through a fiber mat at the top of the sand. Backwashing would have to be done with the filtrate.

The characteristics of the FBU are as follows:

a) filters: Mott 7000–1/2–24–5.0 or Mott 7000–1/2–24–10.0 (10 micron)

b) valves (stainless steel):
  i) 4½" NPT, 24 volt solenoid, normally closed, Telktron
  ii) 3⅜ tubing, ball valve, pressure actuated Whitey 131SR, normally closed, stainless steel
  iii) 1⅜ tubing, ball valve, pressure actuated Whitey 131SR, normally open, stainless steel c) sensors: i) pressure sensor 107 and 108, 0–60 psi Cole Parmer Instrument Co. Model 68001, 4–20 mA output
  ii) proximity sensor 105 and 106, Dwyer capacitive proximity switch model PSC20103

Colloidal components are normally measured by turbidity or light-scattering techniques to give an overall composition or amount of colloidal components. However, colloidal substances include inorganic colloids, such as clays, insoluble salts ($CaSO_4$), or fillers, and organic colloids, such as pitch. Prior art techniques cannot distinguish between these two classes of colloidal matter. Various forms of turbidity measurements, light scattering, and electrokinetic separation are used to measure a quantity of colloidal particles. Using hydrodynamic, electrokinetic separation, or advanced light scattering techniques some information can be obtained about the particle size distribution. These methods are not suitable to distinguish chemically between the different types of particles. The method and the apparatus in accordance with the invention allow to empirically identify and measure a property related to the size, composition, and concentration of a colloidal mixture.

It should be recognized that pitch is a generic term and the composition of an individual pitch particle may vary from relatively pure mixtures of fresh resin and fatty acids to heterogeneous agglomerations of wood extractives, wood-derived lignin and hemicellulose, salt, cationic polymer, and filler particle. The degree that temperature will alter the equilibria between colloidal pitch and dissolved substances is a complicated function of solution conditions and the composition of the pitch particle. For example, our laboratory tests have shown that temperature changes on the same mixture at different pH values produce a different $\Delta$absorbance/$\Delta$temperature relationship. Furthermore, it has been reported that hemicellulose components may stabilize wood colloidal resin (Sundberg, K; Thornton, J.; Holmbom, B.; and Ekman, R. *Journal of Pulp and Paper Science Vol. 22 Number 7*, 1996, Pp J226–J230. Effects of wood polysaccharides on the stability of colloidal wood resin). We have found, however, that variations of pH, and ionic strength that typically occur in a pulp processing or paper making process do not lead to substantial variation in the $\Delta$absorbance/$\Delta$temperature function for a colloidal mixture. It is expected that variation in the concentrations of components that may lead to coagulation and agglomeration may produce pitch particles that are less sensitive changes in temperature. The measurement of $\Delta$absorbance/$\Delta$temperature may be related specifically to the pitch components that are sensitive to temperature change.

The object of the invention requires the use of the variation of an optical property due to a temperature-sensitive phase transition for determining a quantity of a substance that is susceptible to the phase transition. The existence and characteristic temperature of the phase transition is sufficiently important to the technique that the description of these properties becomes an object of the invention. Hence, in order to identify or measure the colloidal mixture it is important to identify a suitable temperature range to obtain measurements.

In accordance with an embodiment of the invention, the steps in the analysis of a colloidal pitch concentration include:

1. Identification of a suitable temperature range and wavelength for the analysis;
   1.1 Identification of regions with maximum change in absorbance with a change in temperature;
   1.2 Identification of a region of a phase transition indicating change between colloidal and dissolved states;
2. Measurement of a dA/dT or the change in an absorbance with respect to temperature;
3. Interpretation of the dA/dT value with respect to a previously defined relationship between the amount of colloidal pitch and the dA/dT value;
4. Defining an relative amount of colloidal pitch as a function of a concentration determined by the dA/dT method and the concentration determined by the total absorbance or turbidity at a given temperature; and
5. A system that has been characterized is simply analyzed following steps 2, 3, and 4.

And, in accordance with an embodiment of the invention, the steps in the identification of a transition temperature or a metastable mixture include:

1. Identification of a suitable wavelengths for the analysis by identifying a region with maximum and minimum change in absorbance with respect to temperature;

2. Measurement of the $dA/dT$, and $d^2A/dT^2$ to determine the point of the minimum rate of change in the slope. The point at which $d^2A/dT^2$ is zero is the temperature that is characteristic of the phase change; and 3. Plot of the ratio of the absorbance at two wavelengths representing maximum and minimum values in the difference or ratio spectra obtained comparison of the absorbance at one temperature from the absorbance at another temperature. This plot provides a means to emphasize the change in the optical properties of the colloid relative to the composition of the mixture as a whole. A change in the slope of this plot indicates the initiation or termination of a phase transition.

Figure 4:
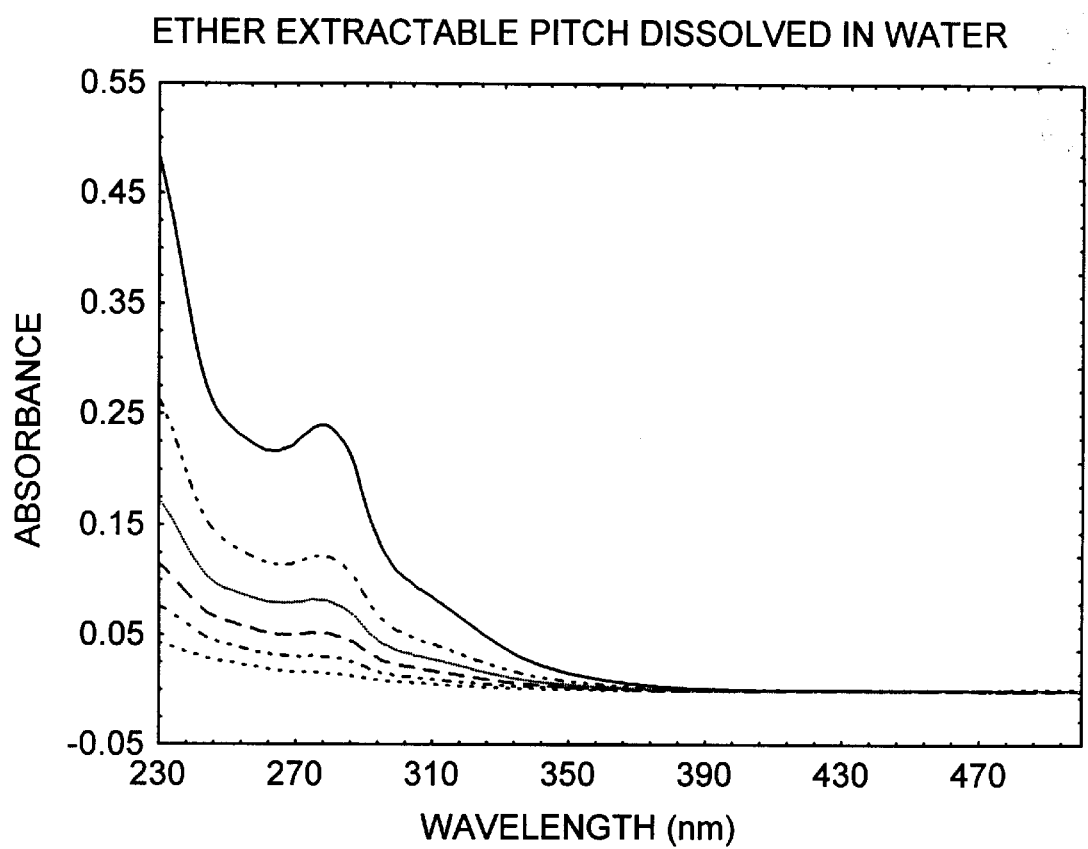
FIG. 4 presents the UV-visible spectra of dissolved spruce/pine extractives obtained by filtration of a colloidal mixture at 0.45 microns.
Figure 5:
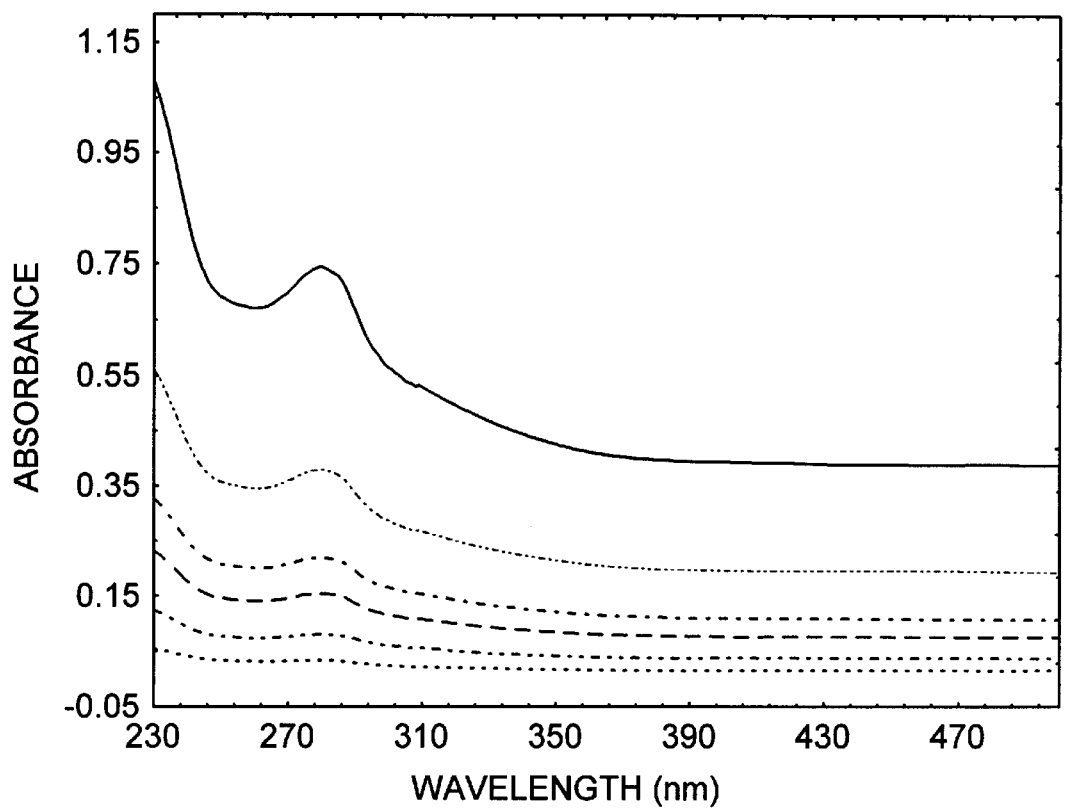
FIG. 5 presents the UV-visible spectrum of dissolved and colloidal spruce/pine extractives at pH 5.4.
Figure 6:
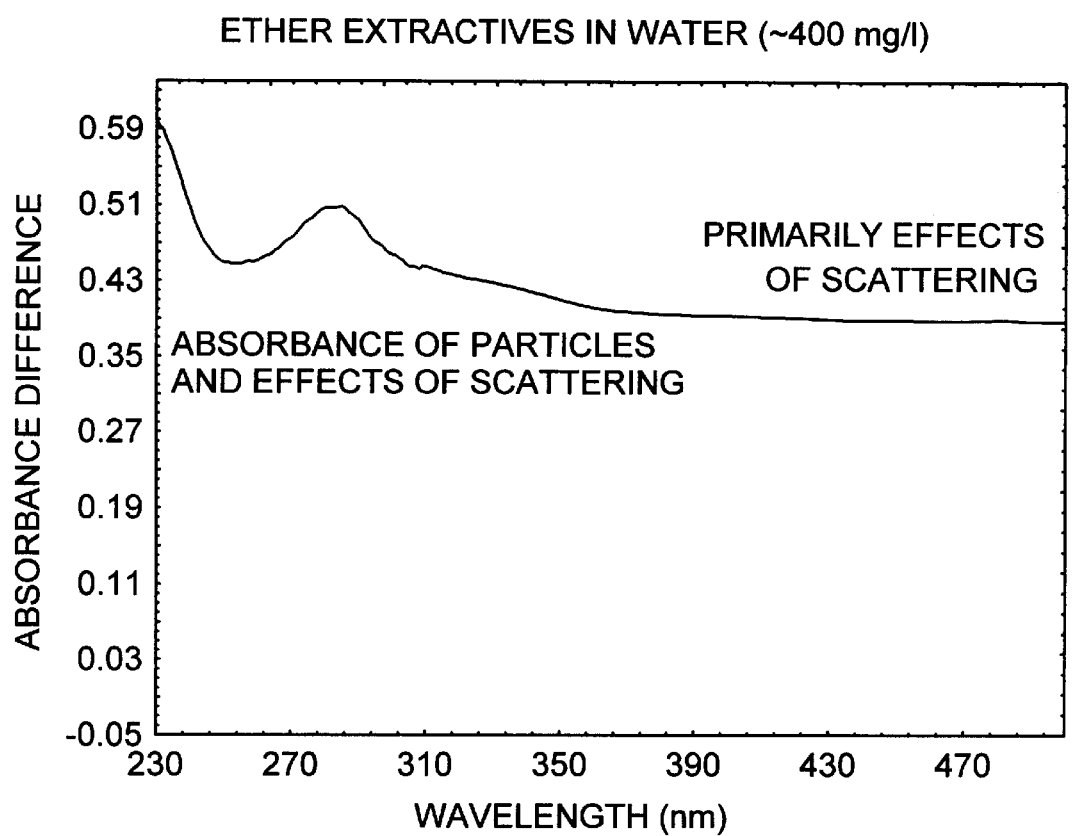
FIG. 6 shows the UV-visible difference spectrum isolating the absorbance of the colloidal pitch.

For example, a t-butyl ether extract of wood resin is obtained by successive extraction of a sample of white water obtained from a spruce/pine thermomechanical pulp mill. The extract is concentrated and then the resin is redispersed in pH 4.85 acetic acid aqueous buffer by sonication. A stock mixture of the dissolved and colloidal wood resin is diluted with buffer to six different concentrations. The UV-visible absorbance spectra of the colloidal mixture are obtained directly from these mixtures at room temperature and are presented in FIG. 5. The colloidal mixtures of different concentrations are filtered with a 0.45 micron syringe filter to obtain solutions of dissolved wood resin and their UV visible spectra are shown in FIG. 4. The signal from dissolved and colloidal matter followed the expected linear relationship with concentration. The attenuation of the signal due to the colloidal substance alone is obtained by subtraction of the signal from the filtered and unfiltered samples. An example for this is presented in FIG. 6. In this example, the signal above 350 nm is taken to primarily represent turbidity or attenuation of the light due to the Mie scattering of the particles. The peaks at 230 and 280 nm indicate that the chromophore containing wood extractives in the colloidal particles adsorbs light.

Figure 7:
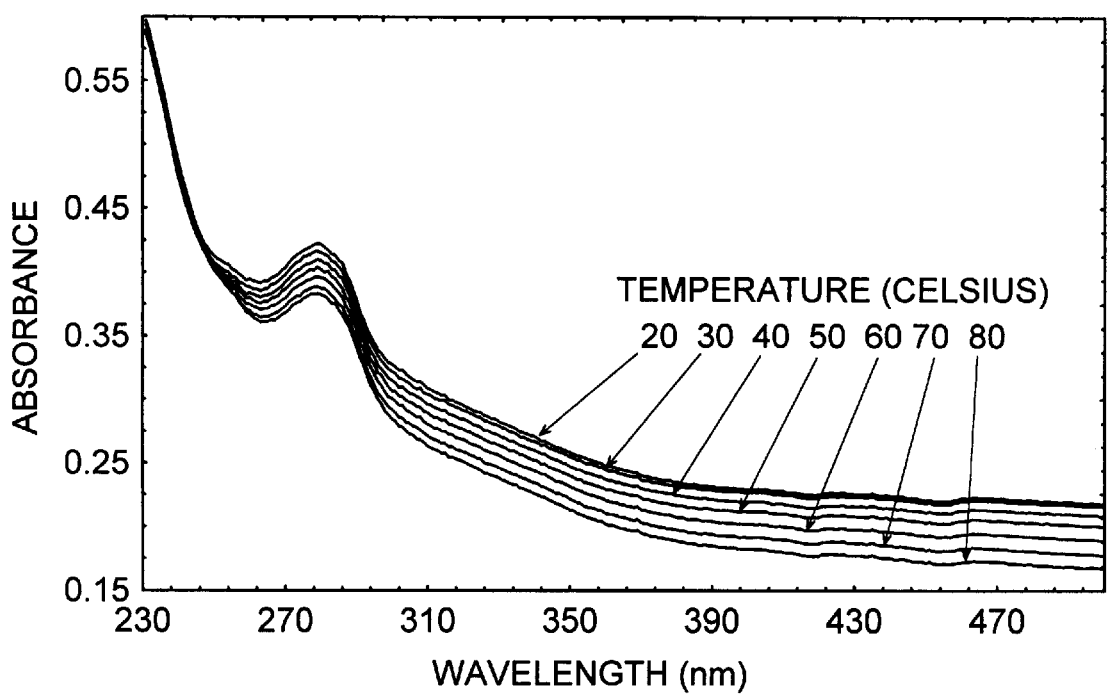
FIG. 7 shows the UV-visible spectra of dissolved and colloidal pitch at pH 5.8 and different temperatures.
Figure 8:
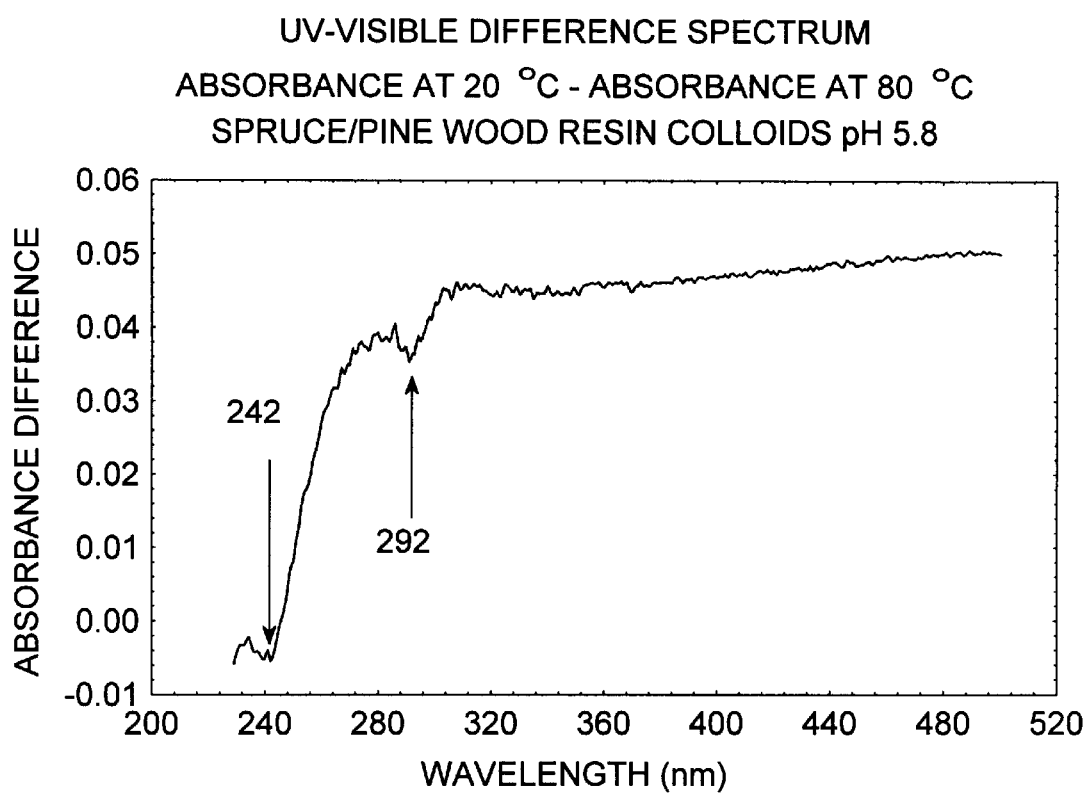
FIG. 8 shows the UV-visible difference spectrum showing the difference between the absorbance at 20° C. and 80° C.
Figure 9:
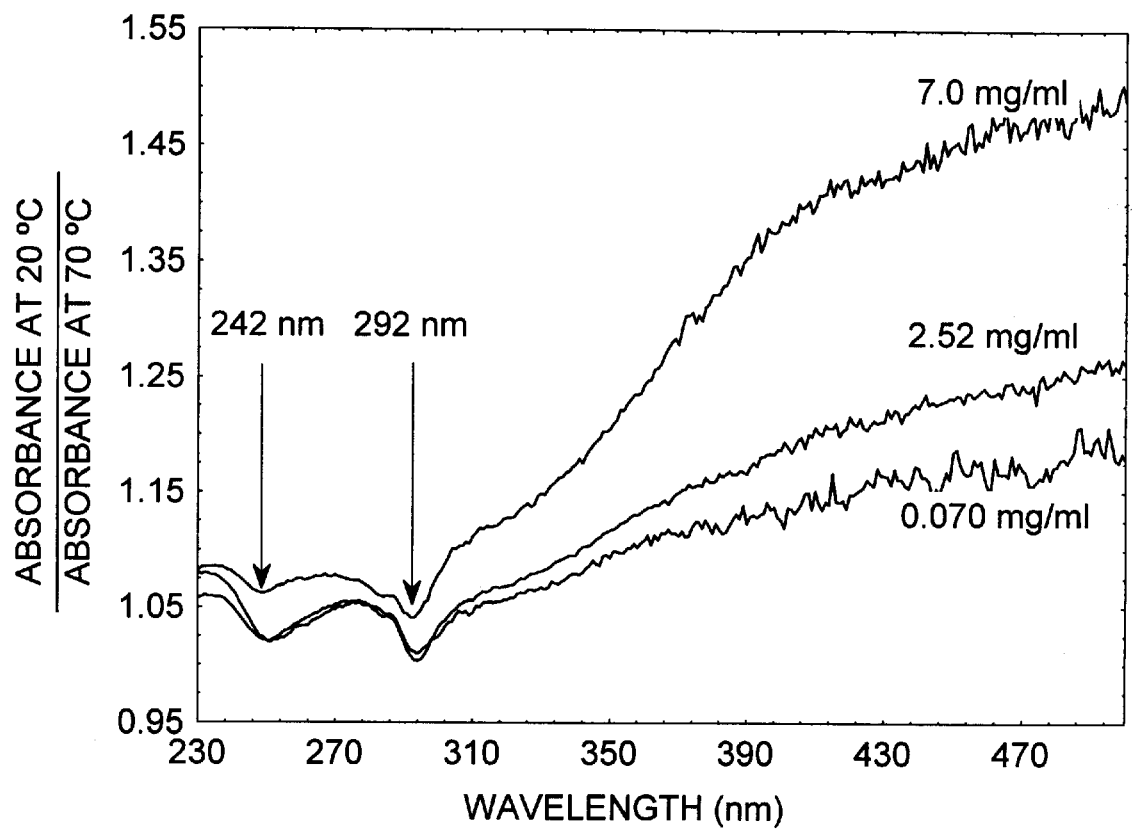
FIG. 9 shows a comparison of UV absorbance at different temperatures compared as ratios.

The temperature dependence of wood resin colloidal mixtures were characterized at different pH values, ionic strengths values, and with different amounts of clay relative to pitch. An example of the temperature dependence of the UV-visible spectrum of wood resin colloid mixtures is shown in FIG. 7. The wavelength dependence of the temperature variation of the UV-visible spectrum can be examined as a difference or a ratio of the spectra taken at two wavelengths as shown in FIG. 8 or FIG. 9. Both methods show a similar pattern. In the UV region, the changes due to a decrease in scattering are compensated by an increase in the UV absorbance. This is likely due to the greater absorbance of the dissolved materials compared to the colloidal materials.

Figure 10A:
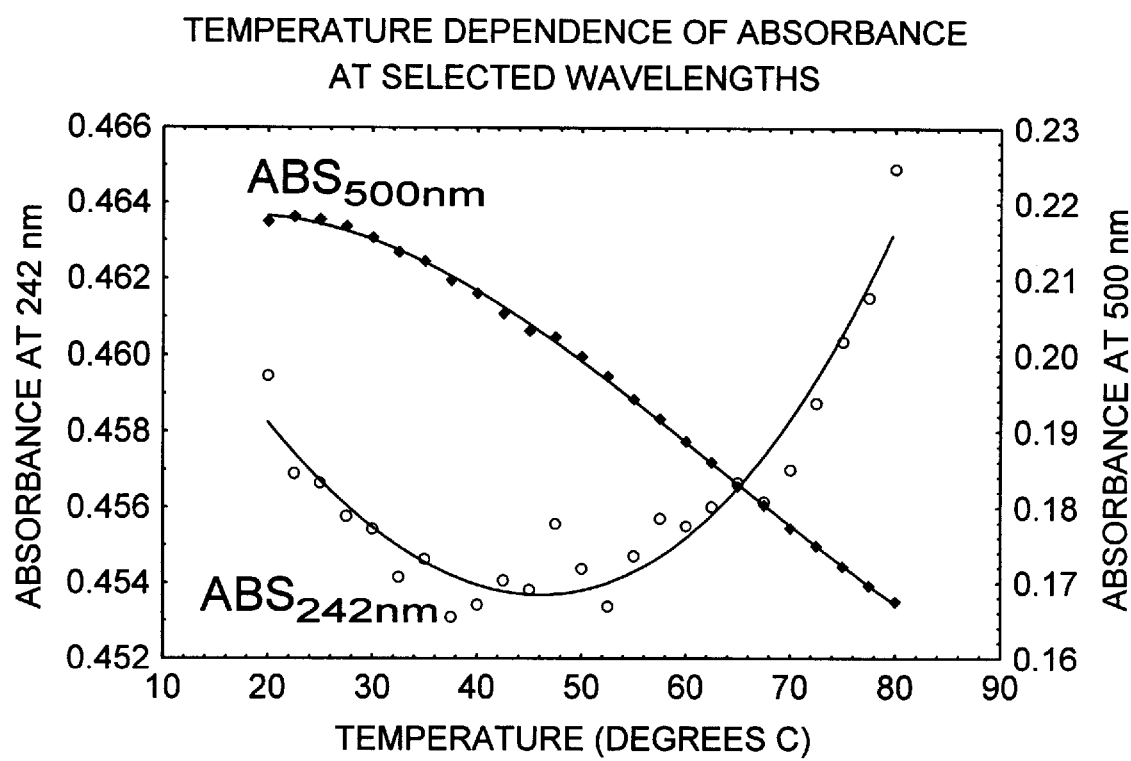
FIG. 10a presents a plot showing the temperature dependence of the UV-visible absorbance at two wavelengths.
Figure 11:
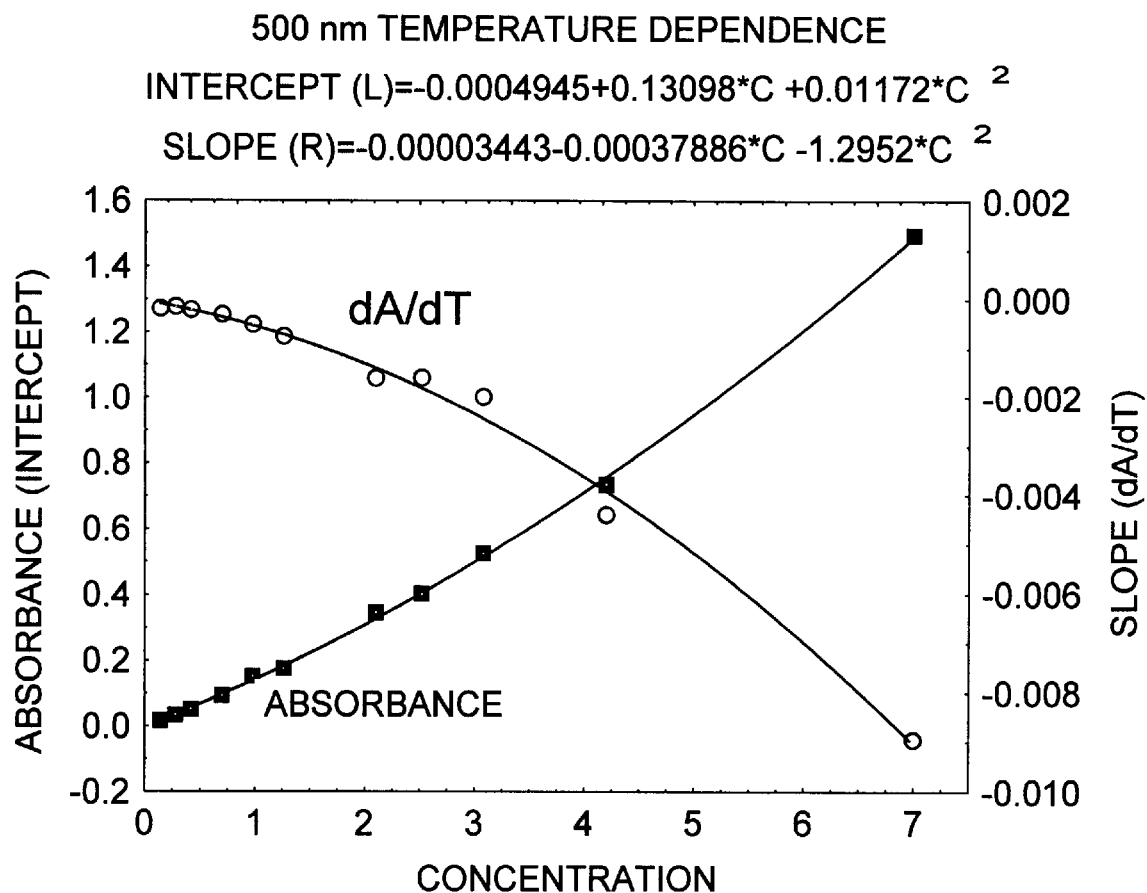
FIG. 11 shows a plot depicting the concentration dependence of the slope (dA/dT) and intercept from a linear regression of the absorbance of a wood-resin suspension obtained at 500 nm and the temperature.

The temperature dependence of the UV absorbance of the extracted pitch is plotted for two wavelengths in FIG. 10*a*. The variation at the 242 nm minimum in the difference spectrum shown in FIGS. 8 and 9 amounts to less than 3% of the total absorbance at that wavelength. On the other hand, the variation at 500 nm is approximately 25% of the absorbance at that wavelength. The variation of the absorbance at 500 nm is substantially linear with changes in temperature ranges between 40° C. and 80° C. It is within this linear region that two measurements provide a slope (dA/dT) that is proportional to the concentration of colloidal pitch. The slope ($dA_{500}/dT$) and intercept $$\left( \lim_{\text{temperature} \to 0} \text{Abs}_{500} \right)$$

are calculated from the temperature dependence of multiple concentrations of colloidal pitch. The slope (dA/dT) and the intercept plotted against the relative concentration are shown in FIG. 11. These original results demonstrate, for the first time, that the temperature variation of the absorbance or turbidity of colloidal pitch is proportional to the amount of pitch in the mixture. The results showing the variation of the intercept with concentration confirm the expected result that the turbidity is a function of the colloid concentration. There is a small non-linearity of the dA/dT with respect to concentration at unusually high concentrations. Measurements are normally made in the concentration region that produces dA/dT values between 0.0 and −0.0025.

Multiple regressions fit to temperature and concentration for absorbance measurements made for UV data at eight representative wavelengths. Exemplary regressions are presented below:

$$A_{500}=0.033499+0.152465*c-0.001180*T-0.004651*c^2$$

$$A_{450}=0.04060+0.195378*c-0.001387*T-0.004470*c^2$$

$$A_{350}=0.084676+0.674637*c-0.002693*T-0.006859*c^2$$

$$A_{300}=0.073323+1.584808*c-0.002703*T-0.013407*c^2$$

$$A_{280}=0.26034+3.054065*c-0.005966*T$$

$$A_{274}=0.22676+3.007551*c-0.006236*T-0.019463*c^2$$

$$A_{250}=0.05867+2.893070*c-0.003785*T-0.039531*c^2$$

$$A_{230}=0.60932+7.328961*c-0.019106*T-0.141523*c^2$$

Multiple regression for UV absorbance at selected wavelengths for TMP white water pitch. The equations are a function of concentration, temperature and the square of the concentration. Regression correlation coefficients of >0.99 were found. The coefficient for the concentration squared indicates interaction between components similar to a second virial coefficient.

In order to make a colloid concentration measurement using this technique, a temperature change must significantly perturb an equilibrium between dissolved and colloidal components. The dissolved and colloidal components must have measurably different properties. The material, solution conditions determine if such a change occurs and the temperature range and wavelength must be selected to best measure the phase change. The optimal wavelength is selected by choosing a maximum or minimum from the ratio or difference of two spectra obtained at two temperatures as shown in FIGS. 8 and 9. The optimal temperature range is chosen by identification of a temperature region around a zero point in the second derivative of the absorbance with respect to temperature. An example of the method of selection of a temperature region follows.

Figure 10B:
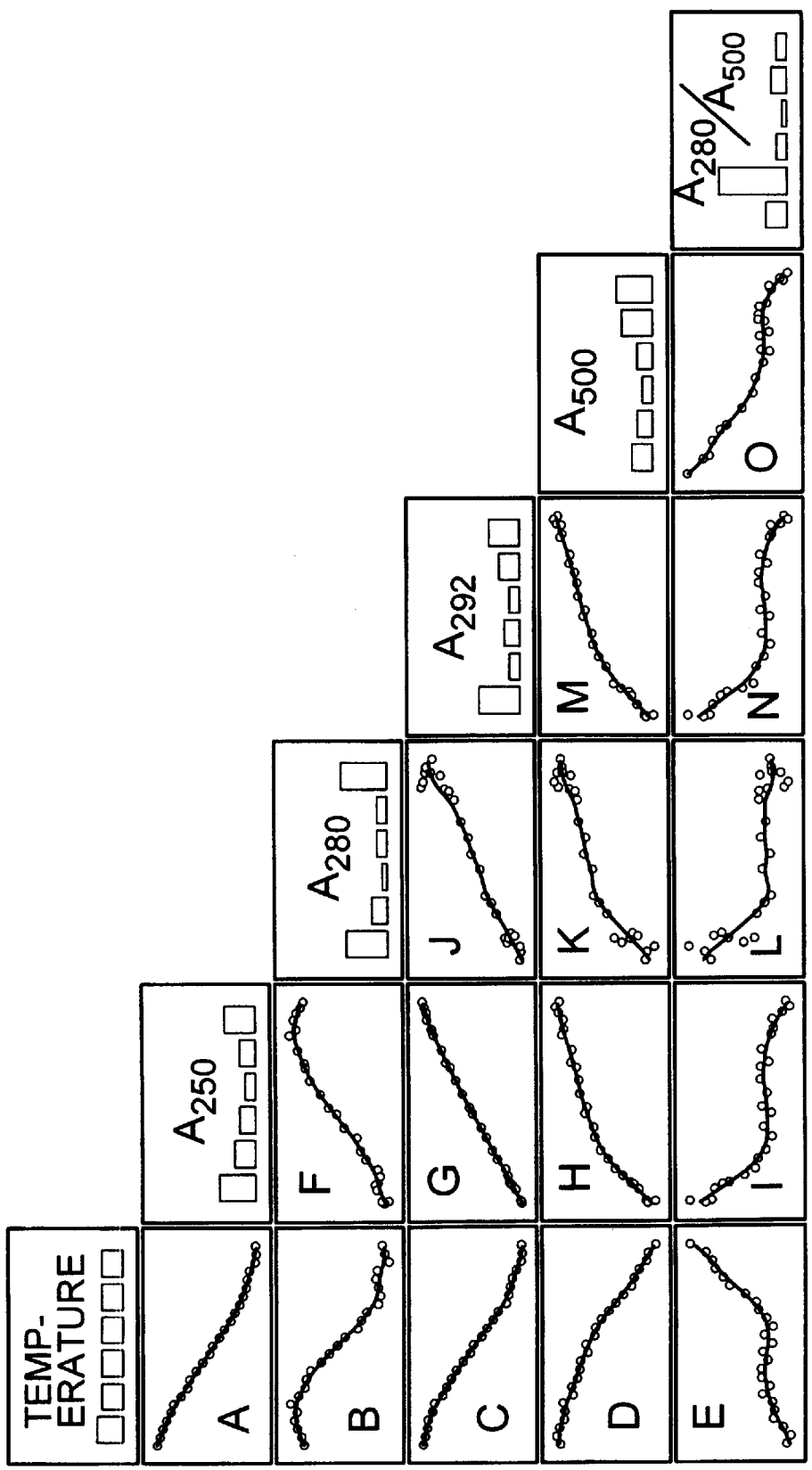
FIG. 10b presents a matrix plot showing the temperature dependence of the UV-visible absorbance of a mixture of wood-resin dissolved and colloidal substances at pH 11.
Figure 10C:
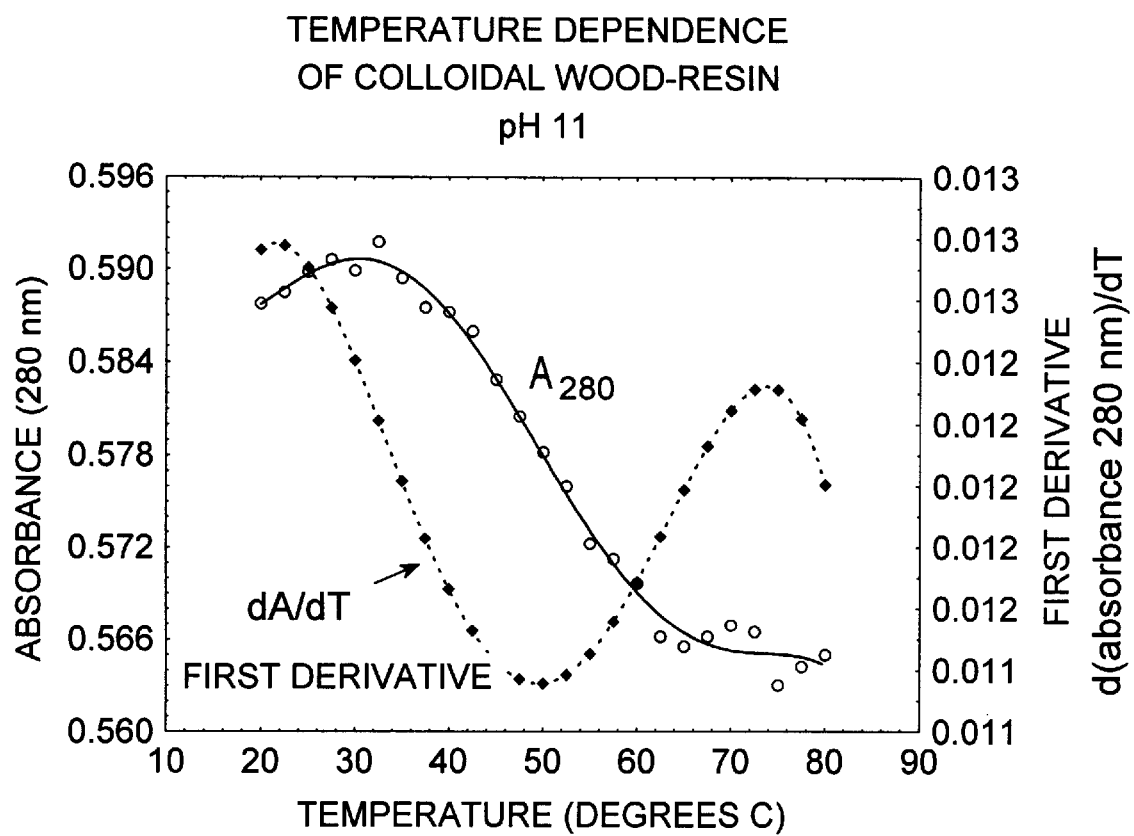
FIG. 10c presents a plot showing the UV absorbance at 280 nm versus temperature showing the first derivative absorbance-temperature relationship.

FIG. 10b shows a matrix plot of the temperature variation of the UV absorbance at pH 11.0. Plots A–D show a variation in the shape of the curves of the absorbance at different wavelengths with respect to temperature (abscissa). At this mixture, there is a relatively complete transition between the dissolved and colloidal components. In particular, the slope falls off significantly at the temperature extremes for the absorbance values at 280 nm. Plot D in FIG. 10b is examined in more detail in FIG. 10c. Inspection of the graph indicates that two measurements made in the region between 20° C. and 40° C. would give different results than measurements made between 40° C. and 60° C. The best region to measure the transition between the colloidal and liquid state is selected from the region where the slope is most constant. This occurs around the central point in the transition that is defined by the minimum in the first derivative function plotted in FIG. 10c. This minimum in the first derivative is the zero point in the second derivative function that occurs, for the data shown in FIG. 10c at 50° C. Secondary zero points in the second derivative occur around 23° C. and 74° C., but these are small regions with very small changes in the absorbance.

The matrix plot presented in FIG. 10b provides further means for the identification of phase changes in colloidal mixtures. In six plots (F, G, H, J, K, M), the absorbance at one wavelength is plotted against another. The linear relationship in plot G shows that the component which provides the dominant temperature variation contributes to both of these wavelengths at all temperatures. Plot H, on the other hand shows that the relative change absorbance is linear in two regions, but the relationship appears to change in an intermediate region. The relative absorbance at two wavelengths may be captured in a ratio as is plotted against temperature in plot E. At the simplest level, the ratio of absorbance values provides a means to inspect the relative change in one component with respect to the change in another component. The linear region with little slope in the central portion of the plot corresponds to a temperature region where changes in the absorbance at 500 nm directly correspond with a change in the absorbance at 280 nm.

Figure 12:
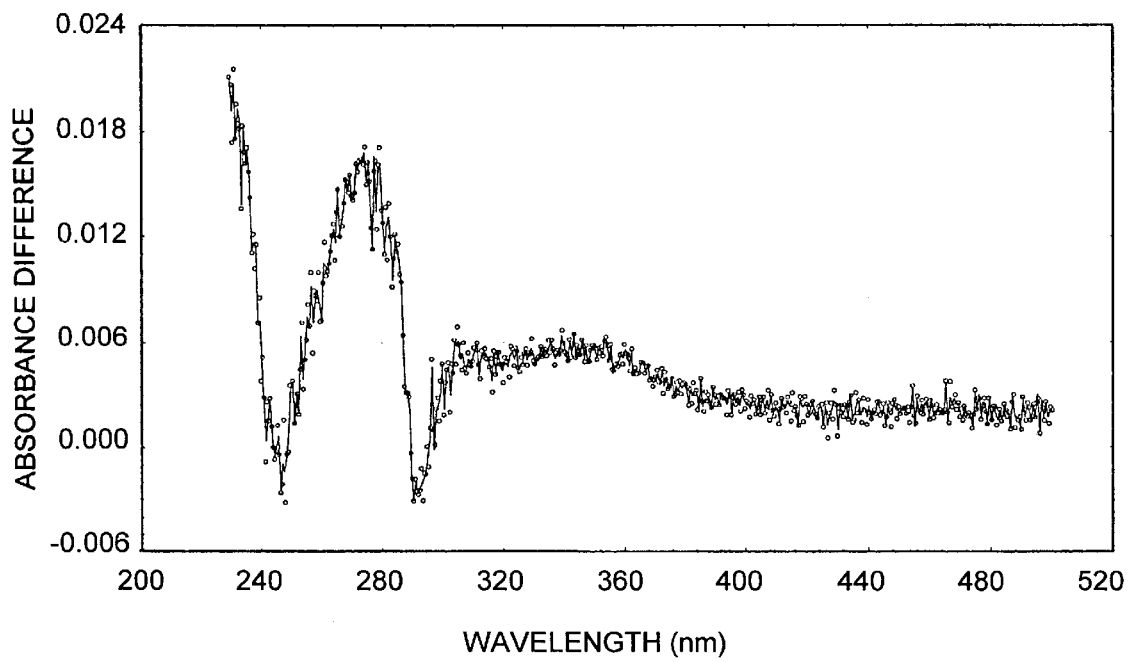
FIG. 12 shows a UV-visible difference spectrum from TMP (thermomechanical pulp) white water.
Figure 13:
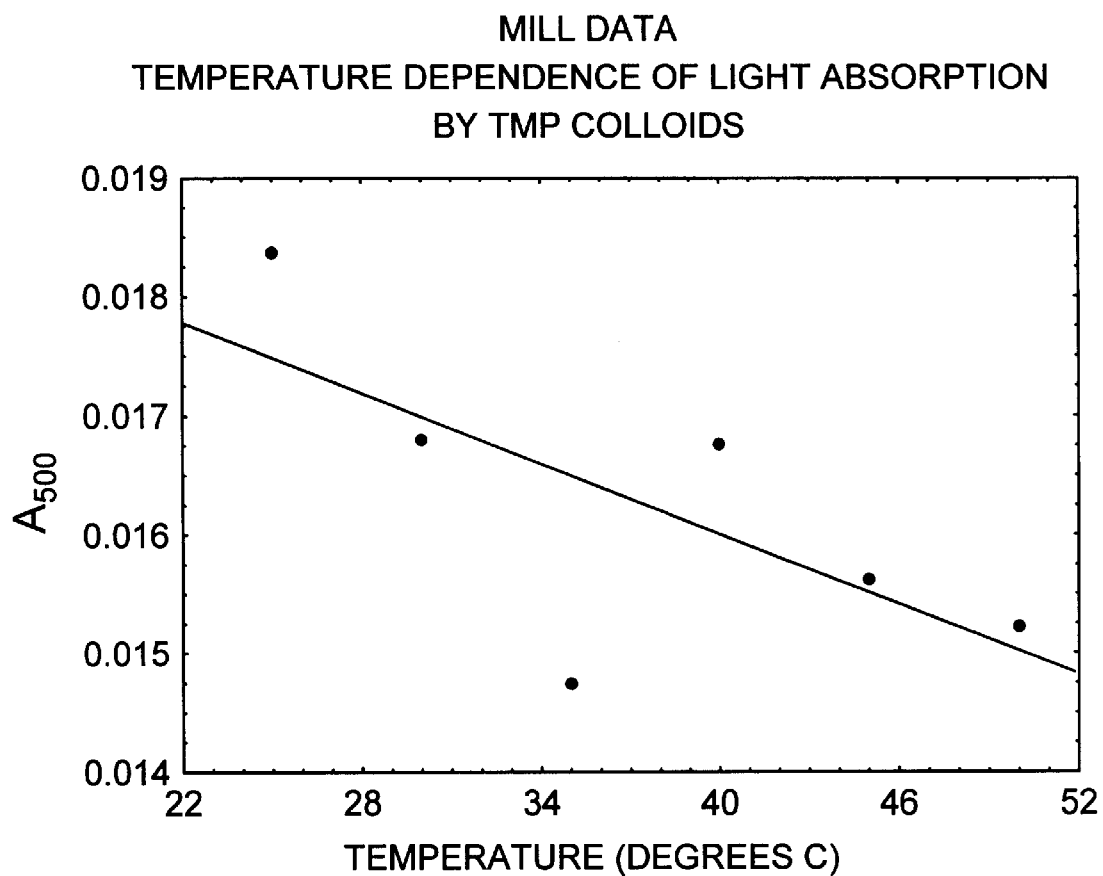
FIG. 13 shows a plot depicting the temperature dependence of the absorbance of a TMP white water at 500 nm.

Additional techniques to obtain accurate and reproducible measurements are learned through experience of applying these measurement techniques at a paper mill. Trial experiments were conducted at a paper mill using white water manually filtered on a Whatman 41 filter paper. This filter paper has a nominal size cut-off of approximately twenty microns. The results are exemplified by the difference spectrum in FIG. 12. This spectrum was obtained with a 1 mm UV cell on a Cary 1 spectrophotometer. This spectrum shows the same minimum points as the difference spectrum in FIGS. 8 and 9. However, in this case the relative absorbance at long wavelengths is much lower. The difference spectrum demonstrates that the temperature change necessary to get accurate measurements must be at least thirty degrees C. Furthermore, a long path UV cell (10 or 20 mm) is used to increase the accuracy of the measurements made at long wavelengths. Scatter in the mill data required to obtain dA/dT is shown in the FIG. 13.

Figure 14:
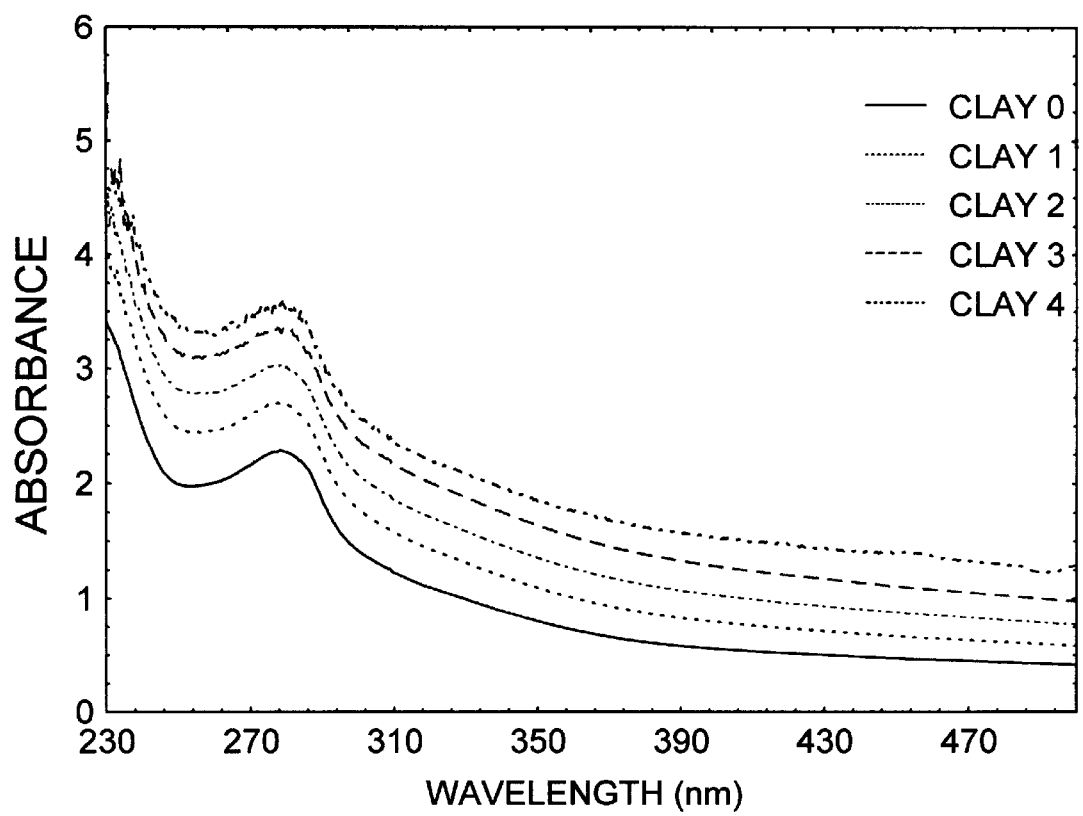
FIG. 14 shows UV-visible spectra of a colloidal mixture of wood-resin with different amounts of added clay.

FIG. 14 shows the spectral effects of adding multiples of a clay concentration to a colloidal pitch solution. The absorbance changes are nearly linear with clay concentration and relatively monotonic with wavelength. Clay and fillers scatter light well and absorb little light compared to colloidal pitch.

Figure 15:
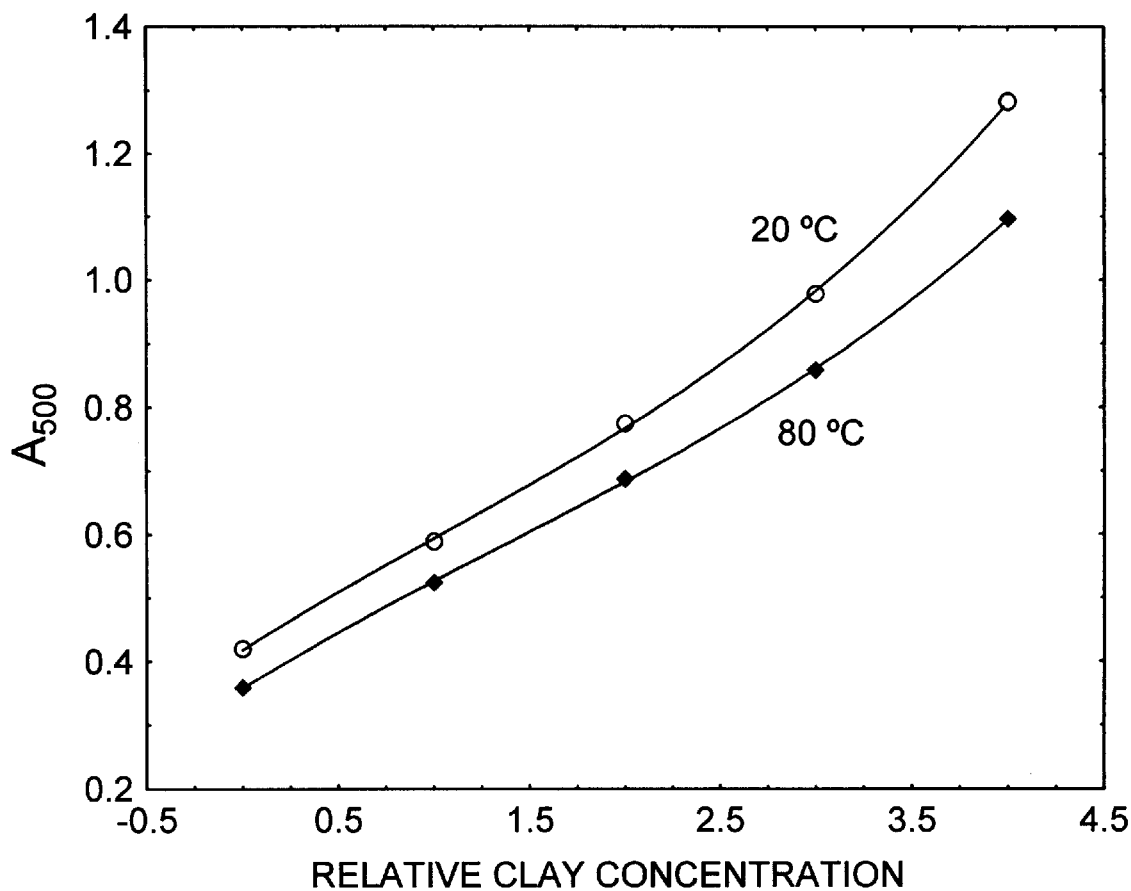
FIG. 15 presents a plot showing the relationship between clay concentration in a pitch/clay mixture and absorbance at 500 nm at two temperatures.

FIG. 15 shows absorbance at 500 nm for different concentrations of clay in a colloidal pitch mixture. The total absorbance is linear with clay concentration. The temperature variation, representing the constant amount of pitch, is shown by the gap between the absorbance at 20° C. and 80° C. Although the size of the gap appears to increase slightly at higher clay concentrations, it is relatively constant given the dramatic range in clay concentrations. Normal variation in clay or filler concentration in a paper mill is usually no more than a factor of two. The data in FIGS. 14 and 15 may be used with a measure of the temperature dependence to first calculate the total amount of the colloids, and then calculate the amount of colloidal pitch, and finally calculate the difference that constitutes colloidal clay and other components that are insensitive to transitions between the colloidal and dissolved phases in the measured temperature range.

In a paper mill situation, it is advantageous to make maximum use of carrying capacity of water resources and still minimize the risk of sudden or catastrophic wet-end chemistry events that lead to deposits and machine fouling associated with poor efficiency and runability. A measurement that provides the paper-maker a better means of predicting the sensitivity of the white water system upsets may be applied to circumvent expensive episodes of deposition on the paper machine. Among diverse causes of wet-end chemistry upsets the sudden variation in white water temperature leading to a wet-end upset is known among papermakers as temperature shock. A sudden change in white water temperature may occur when unusual quantities of fresh water are brought into the water system. In an embodiment, this invention provides a measure of the susceptibility of the water system to a temperature shock. UV ratios track critical behavior better than UV absorbance.

In another embodiment, in agreement with the invention, concentrations of dissolved and colloidal substances that may lead to deposition events are identified. The intention of the papermaker is thus to avoid a metastable state where dissolved components may suddenly come out with a minor fluctuation in operating conditions.

Figure 16:
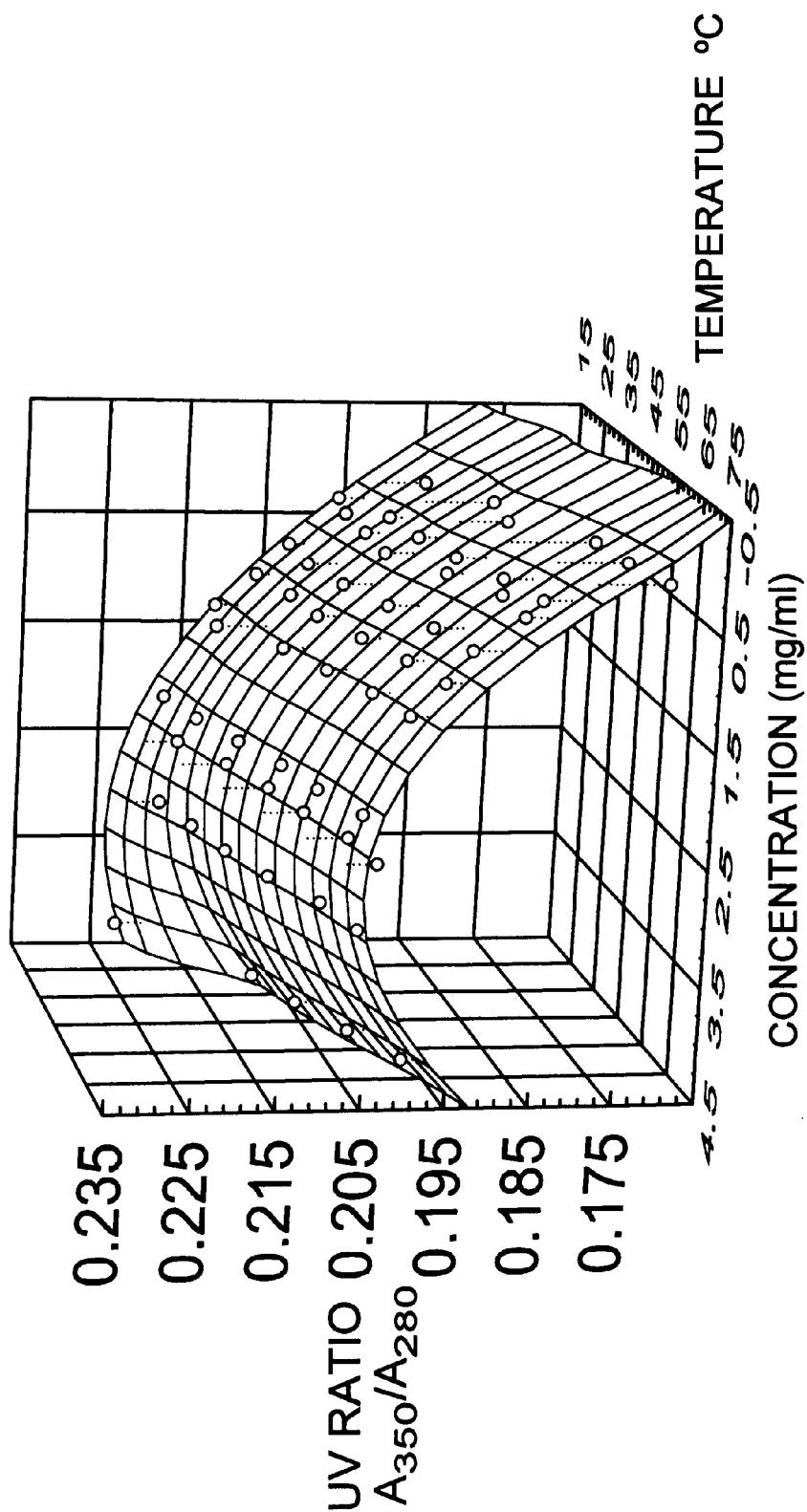
FIG. 16 shows a 3-D plot of the UV ratio $A_{350}/A_{280}$ versus temperature and concentration.
Figure 17:
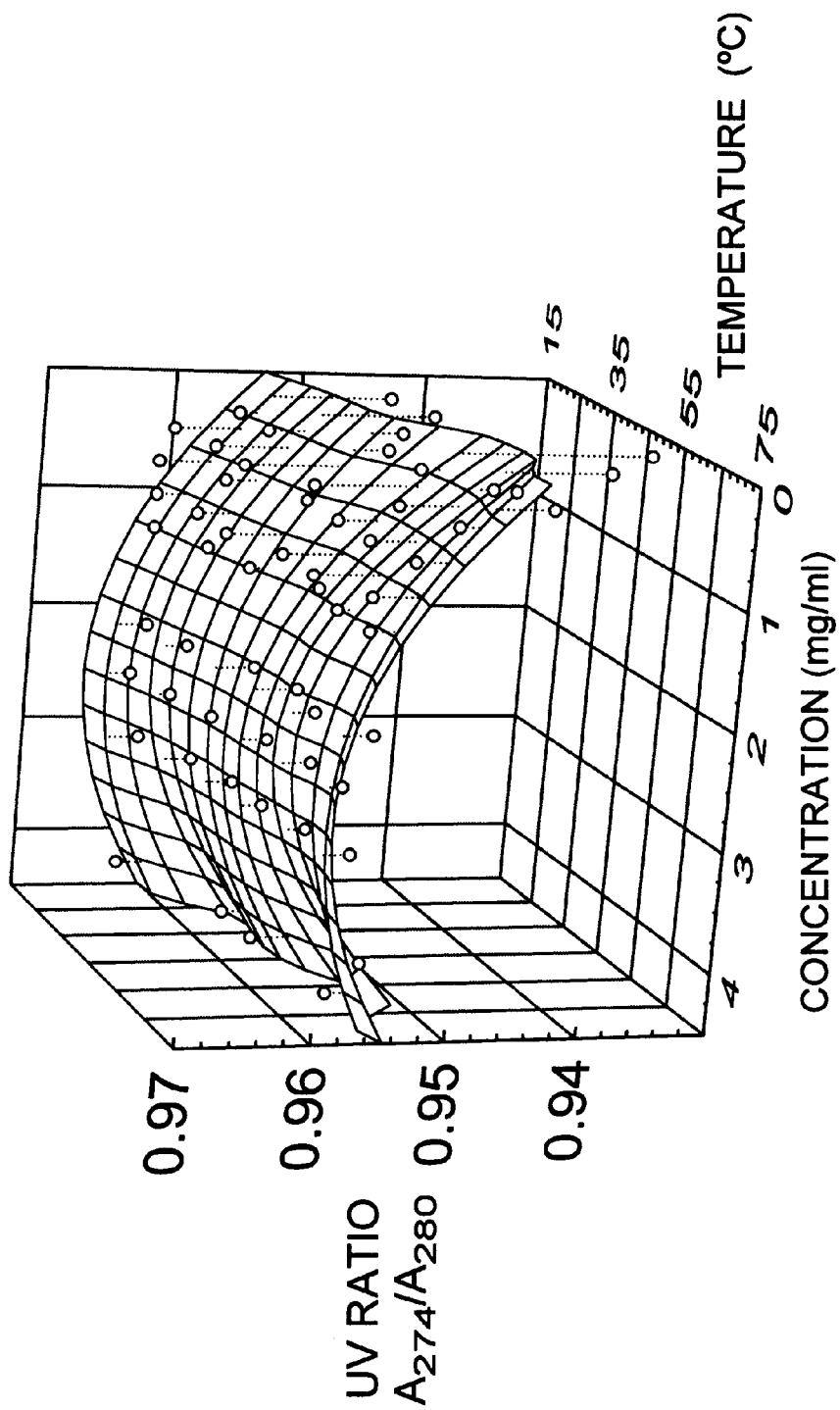
FIG. 17 shows a 3-D plot of UV ratios $A_{274}/A_{280}$ versus temperature and concentration (TDS)
Figure 18:
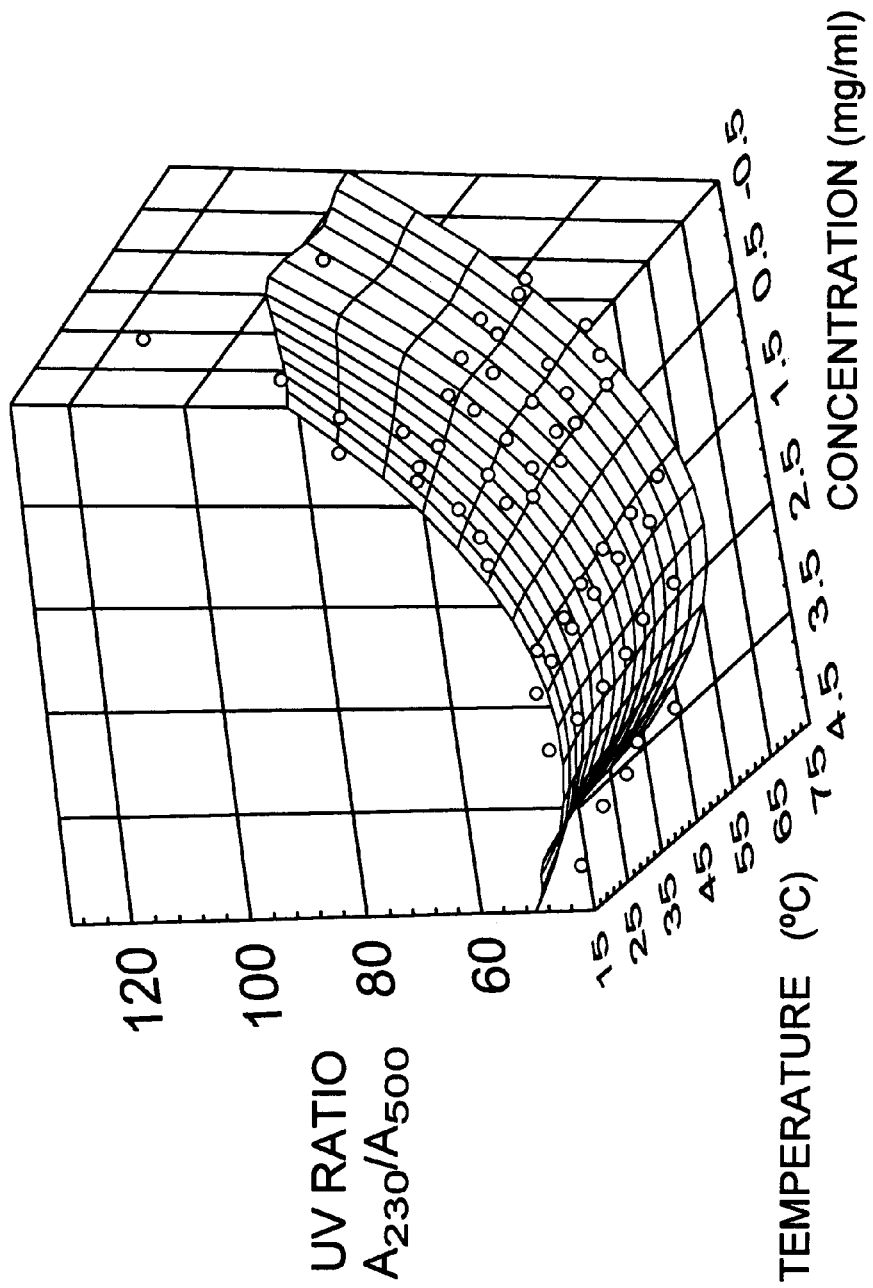
FIG. 18 shows a 3-D plot of UV ratios $A_{230}/A_{500}$ versus temperature and concentration (TDS)
Figure 19:
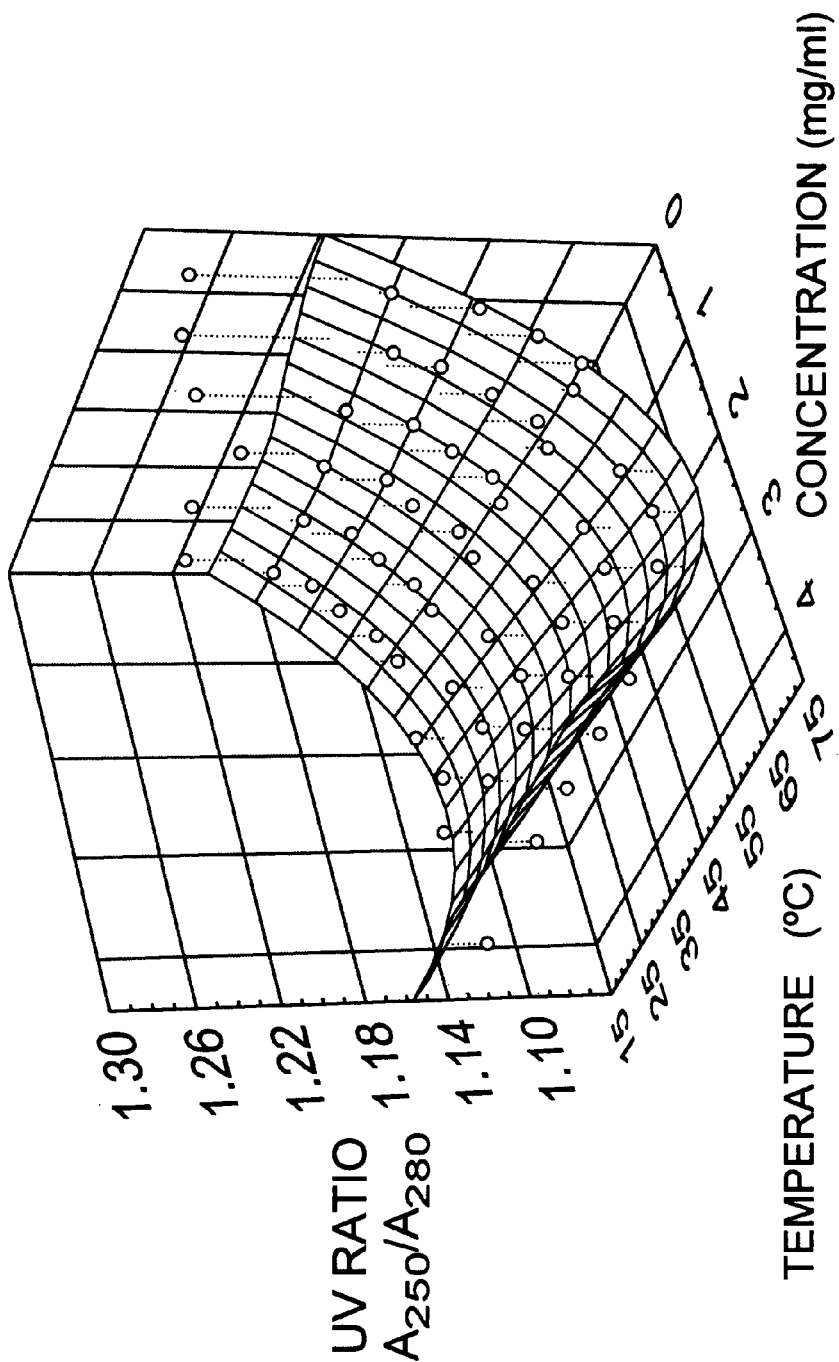
FIG. 19 shows a 3-D plot of UV ratios $A_{250}/A_{280}$ versus temperature and concentration (TDS).

FIGS. 8, 9, 10b, and 12 all show that spectral changes occurring pitch phase transitions are rich sources of information about the transitions occurring. Comparing absorbance values at different wavelengths provides a means of comparing the amount of one component to another component. Examples of three-dimensional plots of temperature, relative dissolved and colloidal substances are provided in FIGS. 16 to 19. Although for the most part UV-visible absorbance shows linear or nearly linear relationships with concentration (TDS) and temperature, the use of UV ratios provides insight into discrete changes in the state of the dissolved and colloidal substances. FIG. 16 shows the ratio $A_{350}/A_{280}$ versus temperature and concentration. The most pronounced change exhibited in this plot is below 1 mg/ml. The relative absence of slope in this graph at high temperatures suggests a change of state that is more discrete than the gradual change at low temperature. The UV ratio $A_{35}/A_{280}$ appears to be a comparison of the contributions of turbidity and UV absorbance. FIG. 17 shows UV ratios of $A_{274}/A_{280}$ versus temperature and concentration (TDS). At high concentrations, this ratio is essentially constant. At low concentrations the ratio decreases. This is interpreted as a red shift due to the comparative effects of solvation in water versus solvation in pitch. FIG. 18 shows UV ratios of $A_{230}/A_{500}$ versus temperature and concentration (TDS). At high concentrations this ratio is essentially constant. Scattering adds proportionately to both long and short wavelengths. At low concentrations, the ratio increases as more extractives are UV absorbing in the dissolved state, but not colloidal. FIG. 19 shows UV ratios of $A_{250}/A_{280}$ versus temperature and concentration (TDS). At high concentrations this ratio is essentially constant indicating no substantial change in the ionization. At low concentrations the ratio increases as more extractives become ionized as they dissolve.

At concentrations above a critical concentration the UV ratio is essentially constant. Ratios that are important include ratios that emphasize ionization (A250/A280, A300/A280); solvent shifts (A300/A292), and a comparison between scattered and UV absorbed light (A500/A230). The absorbance at 292 nm is essentially constant as a function of colloidal or dissolved state.

A scan of selected wavelength ratios versus temperature and identification of points at which the slope changes will identify temperatures that correspond to a transition between dissolved and colloidal components. These temperatures may be used as guides of the system stability at a different temperature.

The above-described embodiments of the invention are intended to be examples of the present invention and numerous modifications, variations, and adaptations may be made to the particular embodiments of the invention without departing from the scope and spirit of the invention, which is defined in the claims.

What is claimed is:

1. A method for identifying and measuring a characteristic of a colloidal mixture comprising the steps of:
    irradiating at least a first portion of the colloidal mixture with light in an ultraviolet-visible region at a first temperature and obtaining a first measurement of a first wavelength within the ultraviolet-visible region, said first measurement for obtaining a measure of one of an absorption, emission and scattering of the first wavelength when said colloidal mixture is irradiated with the light;
    waiting for the temperature of the colloidal mixture to change;
    irradiating at least a second portion of the colloidal mixture with light in an ultraviolet-visible region at a second different temperature and obtaining a second measurement of the first wavelength within the ultraviolet-visible region; said second measurement for obtaining a measure of one of an absorption, emission and scattering of the first wavelength when said colloidal mixture is irradiated with the light; and
    determining the characteristic of the colloidal mixture from a relationship including the first measurement and the second measurement.

2. A method as defined in claim 1 wherein the first portion and the second portion is substantially a same portion.

3. A method as defined in claim 2 wherein the characteristic is a function of a first or second derivative of the at least first and second measurement.

4. A method as defined in claim 3, wherein the characteristic of the colloidal mixture is a measure of an amount of a substance within the colloidal mixture.

5. A method as defined in claim 4, wherein the substance is one of an inorganic colloidal substance and an organic colloidal substance.

6. A method as defined in claim 5, wherein the organic colloidal substance is at least one of a colloidal pitch and a colloidal wood extractive.

7. A method as defined in claim 5, wherein the inorganic colloidal substance is at least one of a clay, a $TiO_2$, carbon black, and a talc.

8. A method as defined in claim 4, wherein the measure of the amount of the substance is for determining a stability of the colloidal mixture.

9. A method as defined in claim 8, wherein the measure of the amount of the substance is for determining the temperature stability of the colloidal mixture.

10. A method as defined in claim 9 wherein a temperature dependency is a measure for an amount of colloidal pitch in the colloidal mixture.

11. A method as defined in claim 4, wherein the measure of the amount of the substance is for identifying a change in a state of the substance, said change including a dissolved state and a colloidal state.

12. A method as defined in claim 2 wherein the initial step comprises the step of filtering the colloidal mixture for substantially removing fiber therefrom.

13. A method as defined in claim 3 wherein a difference between the first temperature and the second temperature is at least 30° C.

14. A method for identifying and measuring a characteristic of a colloidal mixture comprising the steps of:

irradiating at least a first portion of the colloidal mixture with light in an ultraviolet-visible region at a first temperature and obtaining at least a first measurement of a first and a second wavelength within the ultraviolet-visible region, said first measurement for obtaining one of an absorption, emission and scattering of the first wavelength when said colloidal mixture is irradiated with the light;

waiting for the temperature of the colloidal mixture to change;

irradiating at least a second portion of the colloidal mixture with light in an ultraviolet-visible region at a second different temperature and obtaining at least a second measurement of the first and the second wavelength within the ultraviolet-visible region, said second measurement for obtaining one of an absorption, emission and scattering of the second wavelength when said colloidal mixture is irradiated with the light; and determining the characteristic of the colloidal mixture from a relationship including a ratio of the at least first and second measurement.

15. A method as defined in claim 14 wherein the first and the second portion is substantially a same portion.

16. A method as defined in claim 15 wherein the characteristic is a function of a first or second derivative of the at least first and second measurement.

17. A method as defined in claim 16 wherein the characteristic is a measure for one of a critical concentration and a critical temperature for a transition between a dissolved state and a colloidal state.

18. A method as defined in claim 16 wherein the characteristic is a measure of a stability of the colloidal mixture.

19. A method as defined in claim 16 wherein the characteristic is a measure of a composition of the colloidal mixture.

20. A method as defined in claim 19 wherein the colloidal mixture includes an inorganic colloidal component and an organic colloidal component.

21. A method as defined in claim 20 wherein the organic colloidal component is one of a colloidal pitch and a colloidal wood extractive.

22. A method as defined in claim 20 wherein the inorganic colloidal component is one of a colloidal clay, talc, carbon black, and $TiO_2$.

23. A method as defined in claim 19 wherein the colloidal mixture includes a temperature sensitive component and a temperature insensitive component.

24. A method as defined in claim 15 wherein the initial step comprises the step of filtering the colloidal mixture for substantially removing fiber therefrom.

25. A method as defined in claim 15 wherein a suitable temperature difference between the first and the second different temperature is determined by obtaining a first and a second measurement, both at the first and the second wavelength.

26. An apparatus for identifying and measuring a characteristic of a colloidal mixture comprising:

filtration means for substantially removing fiber from the colloidal mixture;

detecting means for obtaining a first measurement and a second measurement of light in an ultraviolet-visible region, said first measurement for obtaining a measure of one of an absorption, emission and scattering of at least a first wavelength of the light at a first temperature when the colloidal mixture is irradiated with the light, and said second measurement for obtaining a measure of one of an absorption, emission and scattering of the first wavelength of the light at a second different temperature when the colloidal mixture is irradiated with the light; and a suitably programmed processor for determining the characteristic of the colloidal mixture from a relationship including the first and second measurement, said characteristic is a function of a first or second derivative of the at least first and second measurement.

27. An apparatus as defined in claim 26 further comprising control means for controlling the detecting means such that measurements are made when the colloidal mixture at predetermined first and second temperatures.

* * * * *

UNITED STATES PATENT AND TRADEMARK OFFICE
CERTIFICATE OF CORRECTION

PATENT NO. : 6,263,725 B1
DATED : July 24, 2001
INVENTOR(S) : Garver et al.

It is certified that error appears in the above-identified patent and that said Letters Patent is hereby corrected as shown below:

Title page,
Item [30], for "Foreign Application Priority Data" should be added claiming priority from, "Canadian Application No: 2,216,046 filed September 18, 1997."

Column 6,
Line 37, "flowthrough" should read -- flow-through --.

Column 13,
Line 36, "$A_{35}/A_{280}$" should read -- $A_{350}/A_{280}$ --.

Column 14,
Line 13, insert the phrase -- said first wavelength is -- prior to the term "one",
Line 14, insert the article -- an -- prior to the term "emission"; insert a -- comma -- after the term "emission"; and insert the article -- a -- prior to the term "scattering",
Line 24, insert the phrase -- said first wavelength is -- prior to the term "one",
Line 25, insert the article -- an -- prior to the term "emission"; insert a -- comma -- after the term "emission",
Line 26, insert the article -- a -- prior to the term "scattering",
Line 45, delete the article -- a -- prior to the abbreviation "$TiO_2$",
Line 46, delete the article -- a -- prior to the term "talc".

Column 15,
Line 6, insert the phrase -- said first wavelength is -- prior to the term "one", insert the article -- an -- prior to the term "emission"; insert a -- comma -- after the term "emission"; and insert the article -- a -- prior to the term "scattering",
Line 16, insert the phrase -- said first wavelength is -- prior to the term "one", insert the article -- an -- prior to the term "emission",
Line 17, insert a -- comma -- after the term "emission", insert the article -- a -- prior to the term "scattering".

Column 16,
Line 22, insert the verb -- is -- after the term "measurement",
Line 23, insert the article -- an -- prior to the term "emission"; insert a -- comma -- after the term "emission"; and insert the article -- a -- prior to the term "scattering", insert the phrase -- light at -- prior to the term "at",
Line 24, delete the phrase "of the light",
Line 26, insert the verb -- is -- after the term "measurement",

UNITED STATES PATENT AND TRADEMARK OFFICE
CERTIFICATE OF CORRECTION

PATENT NO.   : 6,263,725 B1
DATED        : July 24, 2001
INVENTOR(S)  : Garver et al.

It is certified that error appears in the above-identified patent and that said Letters Patent is hereby corrected as shown below:

Column 16 (continued),
Line 27, insert the article -- an -- prior to the term "emission"; insert a -- comma -- after the term "emission"; and insert the article -- a -- prior to the term "scattering", insert the phrase -- light at -- after the phrase "scattering of",
Line 28, delete the phrase "of the light".
Line 39, insert the -- is -- after the term "mixture" and insert the term -- said -- after the term "at".

Signed and Sealed this

Twenty-first Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,263,725 B1
DATED : July 24, 2001
INVENTOR(S) : Garver et al.

It is certified that error appears in the above-identified patent and that said Letters Patent is hereby corrected as shown below:

<u>Title page,</u>
Item [75], the co-inventor's name should read -- Boegh --.

Signed and Sealed this

Twelfth Day of November, 2002

Attest:

Attesting Officer

JAMES E. ROGAN
*Director of the United States Patent and Trademark Office*